United States Patent [19]

Holsheimer et al.

[11] Patent Number: 5,643,330
[45] Date of Patent: *Jul. 1, 1997

[54] MULTICHANNEL APPARATUS FOR EPIDURAL SPINAL CORD STIMULATION

[75] Inventors: Jan Holsheimer, Oldenzaal; Johannes J. Struijk, Rijssen, both of Netherlands

[73] Assignee: Medtronic, Inc., Minneapolis, Minn.

[*] Notice: The term of this patent shall not extend beyond the expiration date of Pat. No. 5,501,703.

[21] Appl. No.: 599,832

[22] Filed: Feb. 12, 1996

Related U.S. Application Data

[62] Division of Ser. No. 185,616, Jan. 24, 1994, Pat. No. 5,501,703.

[51] Int. Cl.⁶ .................................................. A61N 1/05
[52] U.S. Cl. ......................... 607/46; 607/67; 607/117
[58] Field of Search ............................... 607/43, 46, 117, 607/118, 66–70; 128/642

[56] References Cited

U.S. PATENT DOCUMENTS

| | | | |
|---|---|---|---|
| 3,646,940 | 3/1972 | Timm et al. | |
| 3,738,368 | 6/1973 | Avery et al. | |
| 3,822,708 | 7/1974 | Zilber | |
| 3,911,930 | 10/1975 | Hagfors et al. | |
| 4,125,116 | 11/1978 | Fischell | |
| 4,338,945 | 7/1982 | Kosugi et al. | |
| 4,342,317 | 8/1982 | Axelgaard | 607/43 |
| 4,374,524 | 2/1983 | Hudek et al. | |
| 4,379,462 | 4/1983 | Borkan et al. | |
| 4,608,985 | 9/1986 | Crish et al. | |
| 4,628,942 | 12/1986 | Sweeney et al. | |
| 4,649,936 | 3/1987 | Ungar et al. | |
| 4,703,755 | 11/1987 | Tanagho et al. | |
| 4,969,488 | 11/1990 | Byers et al. | 607/118 |
| 5,038,781 | 8/1991 | Lynch | |
| 5,092,329 | 3/1992 | Groupe et al. | 607/66 |
| 5,121,754 | 6/1992 | Mullett | |
| 5,269,304 | 12/1993 | Matthews | 607/46 |
| 5,344,438 | 9/1994 | Testerman et al. | |
| 5,417,719 | 5/1995 | Hull et al. | |
| 5,501,703 | 3/1996 | Holsheimer et al. | 607/46 |

OTHER PUBLICATIONS

"Electrical Stimulation of Pain and Touch" by Robert H. Gibson, Chapter II fron *The Skin Senses* by D.R. Kenshalo, pp. 223–261.

"Generation of Unidirectionally Propagated Action Potentials in a Peripheral Nerve by Brief Stimuli" by Christopher Van Den Honert and J. Thomas Mortimer, *Science*, vol. 206, Dec. 1979, pp. 1311–1312.

(List continued on next page.)

*Primary Examiner*—William E. Kamm
*Assistant Examiner*—George R. Evanisko
*Attorney, Agent, or Firm*—Curtis D. Kinghorn; Harold R. Patton

[57] ABSTRACT

Apparatus for multi-channel transverse epidural spinal cord stimulation uses a multi-channel pulse generator driving a plurality of electrodes mounted near the distal end of a lead. These electrodes are mounted in one or more lines, generally perpendicular to the lead axis, and have a planar surface along one surface of the lead. The lead is implanted adjacent to spinal cord dura mater with the electrodes transverse and facing the spinal cord. Pulses generated by the pulse generator for each channel are not simultaneous but are selectively offset in time and may be of equal or varying amplitude and of equal or varying duration. When the pulses given by the stimulator channels are offset in time and have sufficient amplitude and duration, overlapping areas of stimulation of the spinal area can be obtained. In the overlapping areas of stimulation, the frequency of stimulation is double the frequency of the pulses given by the each stimulator channel separately. Changes in pulse duration and magnitude permit shifting the electrical stimulation field and the resulting paresthesia pattern after installation to accommodate improper lead placement or postoperative dislocation and to minimize unwanted motor responses.

53 Claims, 18 Drawing Sheets

OTHER PUBLICATIONS

"Spinal Cord Stimulation for Chronic, Intractable Pain: Superiority of 'Multi–Channel' Devices" by Richard B. North, et al., 1991 Elsevier Science Publishers B.V. 0304–3959/91/S03.50.

"The 'Failed Back Syndrome' Treated by Percutaneous Spinal Stimulation," 2nd Annual Meeting of American Assoc. of Neurosurgery, San Diego, California, 1986; 7pp.

"Mapping of Sensory Responses to Epidural Stimulation of the Intraspinal Neural Structures in Man" by Giancarlo Barolat, M.D., et al., *J. Neurosurg.*, vol. 78, Feb. 1993, pp. 233–239.

"Multielectrode Spiral Cuff for Ordered and Reversed Activation of Nerve Fibres" by J. Rozman, et al., *J. Biomed. Eng*, Mar. 1993, vol. 15.

"A Theoretical Study of Epidural Electrical Stimulation of the Spinal Cord—Part II: Effects on Long Myelinated Fibers" by Barry Coburn, IEEE Transactions on Biomedical Engineering, vol. BME–32, No. 11, Nov. 1985.

"A Theoretrical Study of Epidudral Electrical Stimulation of the Spinal Cord—Part I: Finite Element Analysis of Stimulus Fields" by Barry Coburn and Wing Kee Sin, IEEE Transactions on Biomedical Engineering, vol. BME–32, No. 11, Nov. 1985.

"Spinal Stimulation: Statistical Superiority of Monophasic Stimulation of Narrowly Separated, Longitudinal Bipoles Having Rostral Cathodes" by Jay D. Law, Proc. of Amer. Soc. Stereoctatic and Functional Neurosurgery, Durham, N.C., 1983, *Appl. Neurophysiol.* 46, pp. 129–137 (1983).

"Targeting a Spinal Stimulator to Treat the 'Failed Back Surgery Syndrome'" by Jay D. Law, Proceedings of the Meeting of the American Society for Stereotaltic Functional Neurosurgery, Montreal 1987, *Appl. Neurophysiol.* 50, pp. 437–438 (1987).

"Simulation of Multipolar Fiber Selective Neural Stimulation Using Intrafascicular Electrodes" by J.H. Meier, et al., IEEE Transactions on Biomedical Engineering, vol. 39, No. 2, Feb. 1992, pp. 122–134.

"Reduction of Electrical Interaction in Auditory Prostheses" by Brent Townshend and Robert L. White, IEEE Transactions on Biomedical Engineering, vol. BME–34, No. 11, Nov. 1987, pp. 891–897.

"Selective Control of Muscle Activation with a Multipolar Nerve Cuff Electrode" by Claude Veraart, et al., IEEE Transactions on Biomedical Engineering, vol. 40, No. 7, Jul., 1993, pp. 640–653.

"A Nerve Cuff Technique for Selective Excitation of Peripheral Nerve Trunk Regions" by James D. Sweeney, et al., IEEE Transactions on Biomedical Engineering, vol. 37, No. 7, Jul. 1990, pp. 706–715.

"Failed Back Surgery Syndrome: 5–Year Follow–Up after Spinal Cord Stimulator Implantation" by Richard B. North, et al., *Neurosurgery*, 28, 5, May 1991, pp. 692–699.

"Multifactorial Analysis of Epidural Spinal Cord Stimulation" by Giancaro Barolat, et al., *Stereotact Funct Neurosurg* 1991, 56, pp. 77–103.

"Recruitment of Dorsal Column Fibers in Spinal Cord Stimulation: Influence of Collateral Branching" by Struijk, et al., IEEE Transactions on Biomedical Engineering, vol. 39, No. 9, Sep. 1992, pp. 903–912.

"Electrode Geometry and Preferential Stimulation of Spinal Nerve Figers Having Different Orientations: A Modeling Study" by Jan Holsheimer and Johannes J. Struijk, Proc. 14th Ann Int Conf IEEE Eng in Med & Biol Soc, Paris (France) 1992; pp. 1374–1375.

"Selective Activation of Small Motor Axons by Quasitrapezoidal Current Pulses" by Zi–Ping Fang and J. Thomas Mortimer, IEEE Transactions on Biomedical Engineering, vol. 38, No. 2, Feb. 1991, pp. 168–174.

"A Method to Effect Physiological Recruitment Order in Electrically Activated Muscle" by Z–Ping Fang and J. Thomas Mortimer, IEEE Transactions on Biomedical Engineering, vol. 38, No. 2, Feb. 1991, pp. 175–179.

"Orderly Stimulation of Skeletal Muscle Motor Units with Tripolar Nerve Cuff Electrode" by Richard Baratta, et al., IEEE Transactions on Biomedical Engineering, vol. 36, No. 8, Aug. 1989, pp. 836–843.

"How Do Geometric Factors Influence Epidural Spinal Cord Stimulation? A Quantitative Analysis by Computer Modeling" by J. Holsheimer, Ph.D. and J.J. Struijk, Ph.D., *Stereotactic and Functional Neurosurgery*, 1991; 56, pp. 234–249.

"Contact Combinations in Epidural Spinal Cord Stimulation—A Comparison by Computer Modeling" by J. Holsheimer, J.J. Struijk, N.J.M. Rijkhoff, *Stereotactic and Functional Neurosurgery*, 1991; 56:220–233.

"Parethesia Thresholds in Spinal Cord Stimulation: A Comparison of Theoretical REsults with Clinical Data" by Johannes J. Struijk, et al., IEEE Transactions on Rehabilitation Engineering, vol. 1, No. 2, Jun. 1993, pp. 101–108.

"Excitation of Dorsal Root Fibers in Spinal Cord Stimulation: A Theoretical Study" by Johannes J. Struijk, et al., IEEE Transactions on Biomedical Engineering, vol. 40, No. 7, Jul. 1993, pp. 632–639.

"Differential electrical excitation of the auditory nerve," by R.C. Black and G.M. Clark, *Journal of Acoustical Society of America*, 67(3), Mar. 1980, pp. 868–874.

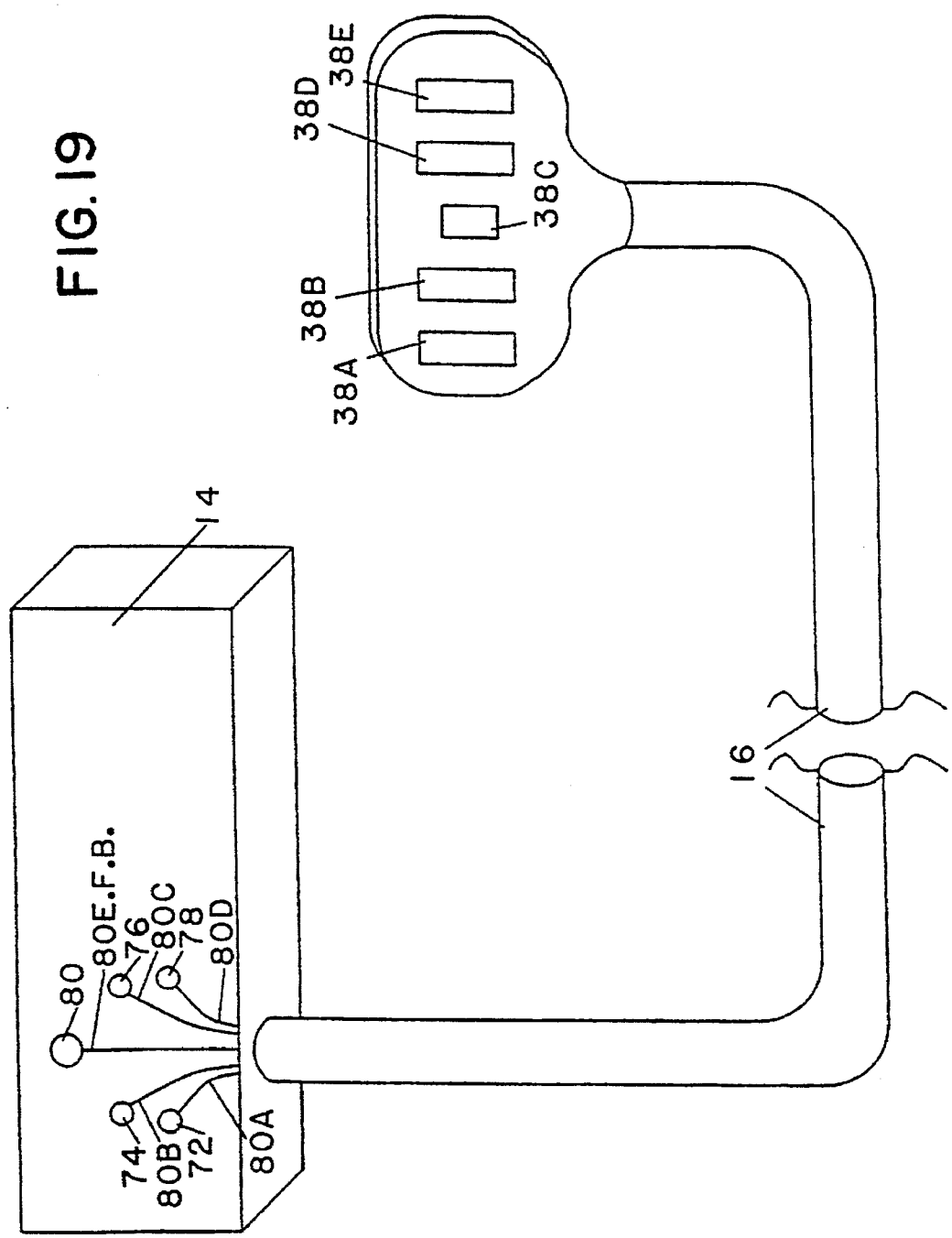

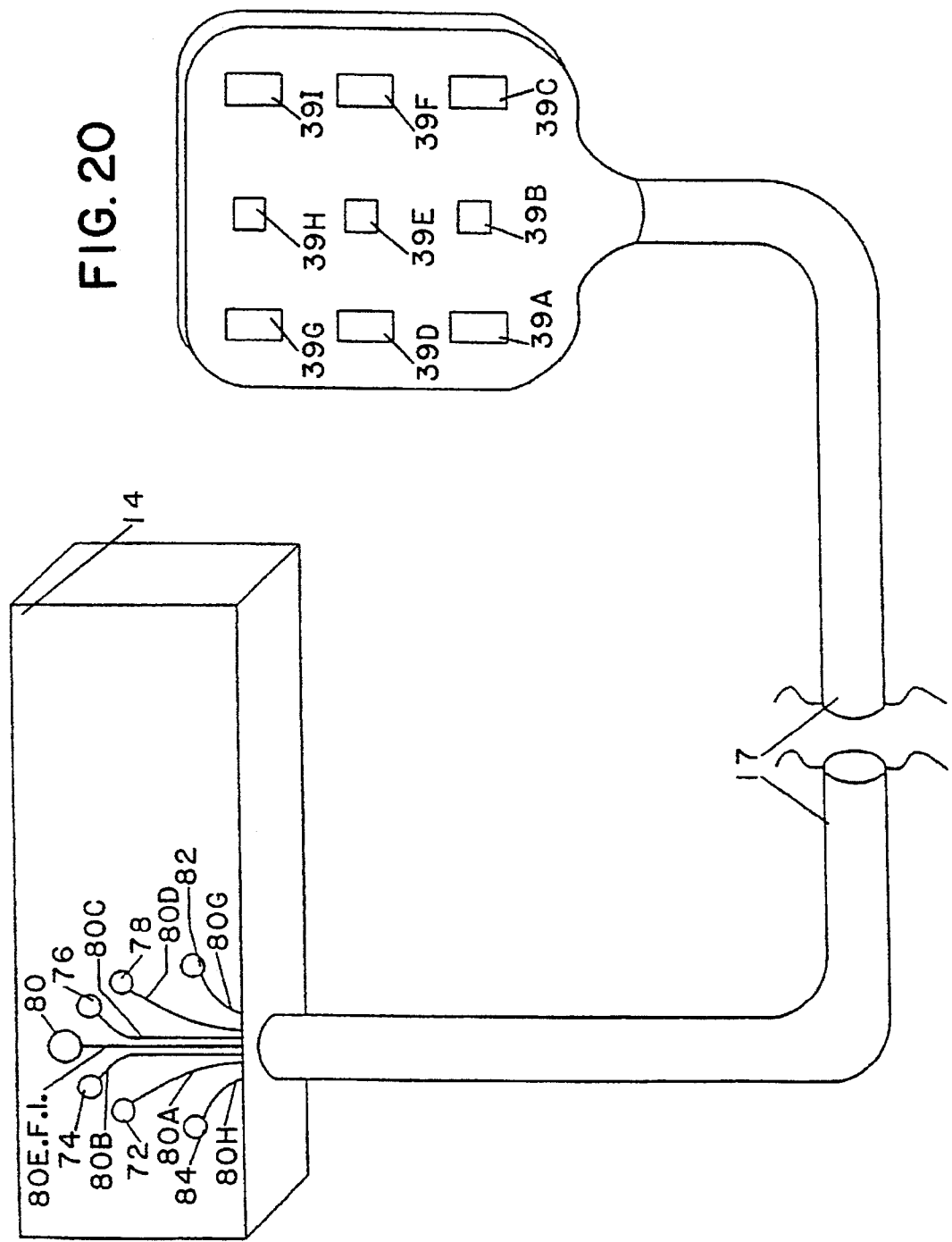

MULTICHANNEL APPARATUS FOR EPIDURAL SPINAL CORD STIMULATION

This application is a divisional of application application Ser. No. 08/185,616 filed on Jan. 24, 1994 now U.S. Pat. No. 5,501,703.

BACKGROUND OF THE INVENTION

1. Field of the Invention

This invention relates to apparatus and method for electrically stimulating a spinal cord. More specifically, this invention relates to an apparatus and method for changing the intensity and location of resulting spinal cord stimulation by changing the pulse parameters of at least two separate voltage or current controlled sources applied to in line electrodes transverse to the spinal cord axis.

2. Description of the Prior Art

In epidural spinal cord stimulation (ESCS) two major practical problems reduce the efficacy of this therapy. One is the difficulty of directing the stimulation induced paresthesia to the desired skin areas and the other is the problem of motor responses to the stimulation, which reduces the amplitude range of the stimulation. It is generally agreed that in ESCS, for chronic pain, paresthesia should cover the whole pain region. With present stimulation methods and equipment only highly skilled and experienced surgeons are able to position the lead in such a way that the desired overlap is reached and desired results are obtained over time. It is difficult to focus the stimulation on the desired region during surgery and, with single channel approaches, impossible to refocus it afterwards, even though some small readjustments can be made by selecting a different contact combination, pulse rate, pulse width or voltage.

Especially the possibility of refocusing paresthesia after surgery would be highly desirable because, even if during surgery paresthesia covers the pain area perfectly, the required paresthesia pattern often changes later. This may be caused by such things as lead migration or histological changes, such as the growth of connective tissue around the electrode. The problem of lead placement has been addressed by U.S. Pat. No. 5,121,754 by the use of a lead with a deformable distal shape.

Using mathematical modeling we have discovered that the superposition of potential fields due to simultaneous stimulation by multiple pulse generators and connected electrodes will result in a significant change in the size and shape of the stimulated spinal cord area. This means that post-operative changes in stimulation fields can be obtained by selective parametric changes in the pulse generator outputs. Such changes in the stimulated spinal cord area will not only improve pain suppression but unwanted motor responses will be minimized or eliminated as well. These changes in stimulated area are impossible to obtain using a single channel stimulation.

U.S. Pat. No. 3,379,462 provides multiple electrodes but does not address the problem of post operative field changes and does not provide superimposed fields due to multiple channel stimulation.

U.S. Pat. No. 3,646,940 provides electrical means for locally stimulating masses of electrically excitable tissue using several pulse generators which are electrically connected to multiple electrodes at distant sites. The problem addressed includes bladder evacuation where an electrical pulse will contract the bladder but simultaneously contract the sphincter thus inhibiting evacuation. This problem is overcome by the use of a second time shifted electrical pulse to inhibit the sphincter response. This approach using separate bipolar electrodes to stimulate a nerve at multiple sites can not address the problem of the field superposition necessary to shift a stimulation field with respect to the spinal cord. This is because the stimulation sites according to this teaching are so far apart that the potential fields do not overlap, and thus will not give another field by linear superposition even if pulses are applied simultaneously to the two bipolar electrodes. Moreover, the precise and stable positioning of bipolar electrodes relative to each other necessary to establish desired and known field superposition is not obtainable by surgical implantation of separate electrode pairs. Therefore, this patent does not address the use of varying superimposed fields to vary the population of recruited nerve fibers.

The problems of directing stimulation induced paresthesia to desired skin areas, of unwanted motor responses to stimulation, of correcting for lead migration or incorrect positioning during surgery, and of making significant post-operative field changes have not been solved by existing apparatus and methods.

SUMMARY OF THE INVENTION

The apparatus of this invention provides a number of superimposed current generated electrical fields for epidural spinal cord stimulation. The apparatus uses a multi-channel neurological pulse generator which provides independently controlled voltage or current pulses. A lead connected to the pulse generator has electrodes at the distal end corresponding to the number of channels. The lead is implanted a few mm apart from the spinal cord with the electrode array transverse and facing the spinal cord. The pulses given by the stimulator channels are selectably simultaneous or alternate in time, are selectably equal or different in amplitude, or both. These capabilities permit shifting the electrical field after implantation to optimize the paresthesia effects or to eliminate unwanted motor responses. This use of multiple, superimposed potential fields, generated by transverse combinations of electrodes, results in different and variable stimulated spinal cord areas as compared to a single field, and thus provides a better controllable paresthesia effect. The various means provided for shifting and changing the stimulated spinal area postoperatively, whether used individually or collectively, permit tailoring the stimulated area to a particular individual's spinal cord site.

In particular, when the pulses given by the stimulator channels alternate in time and have sufficient amplitude and duration, overlapping areas of stimulation of the spinal area can be obtained. In the overlapping areas of stimulation, the frequency of stimulation is double the frequency of the pulses given by each of the stimulator channels separately.

BRIEF DESCRIPTION OF THE DRAWINGS

FIG. 19 shows a schematic of the pulse generator driving a first embodiment of the lead.

FIG. 20 shows a schematic of the pulse generator driving a second embodiment of the lead.

DETAILED DESCRIPTION OF THE PREFERRED EMBODIMENTS

Figure 1:
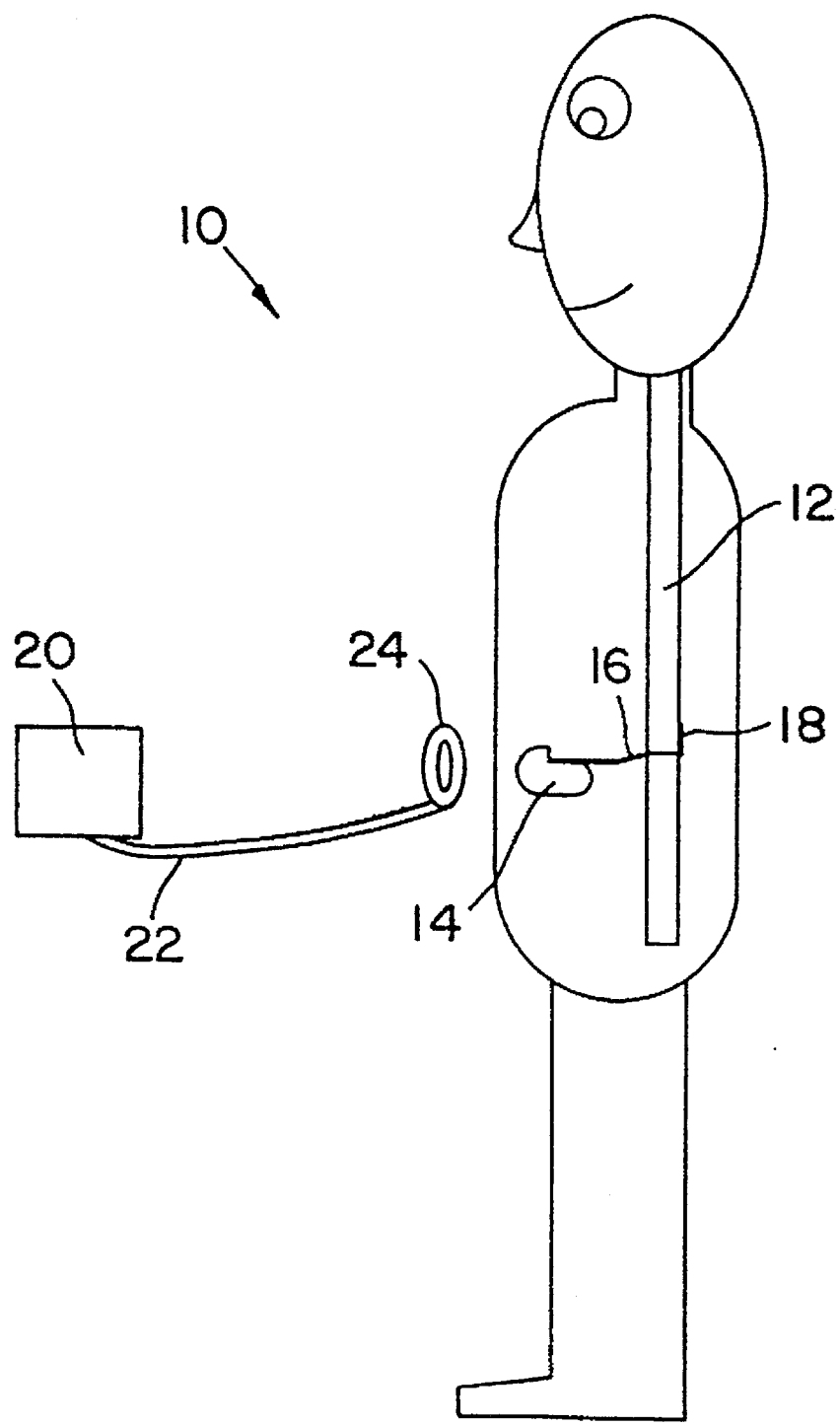
FIG. 1 is a schematic view of a patient with an implanted neurological stimulation system employing the present invention.

FIG. 1 is a schematic view of a patient 10 having an implant of a neurological stimulation system employing the present invention to stimulate spinal cord 12 of the patient. The preferred system employs implantable pulse generator 14 to produce a number of independent stimulation pulses which are sent to spinal cord 12 by insulated lead 16 and coupled to the spinal cord by electrodes located at point 18.

Implantable pulse generator 14 preferably is an ITREL IIR implantable pulse generator available from Medtronic, Inc. with provisions for multiple pulse outputs which are selectably either simultaneous or with one shifted in time with respect to the other, and which are selectably of independently varying amplitudes. This preferred system employs programmer 20 which is coupled via conductor 22 to radio frequency antenna 24. This permits attending medical personnel to select the various pulse output options after implant using radio frequency communications. While the preferred system employs fully implanted elements, systems employing partially implanted generators and radio-frequency coupling may also practice the present invention.

Figure 2:
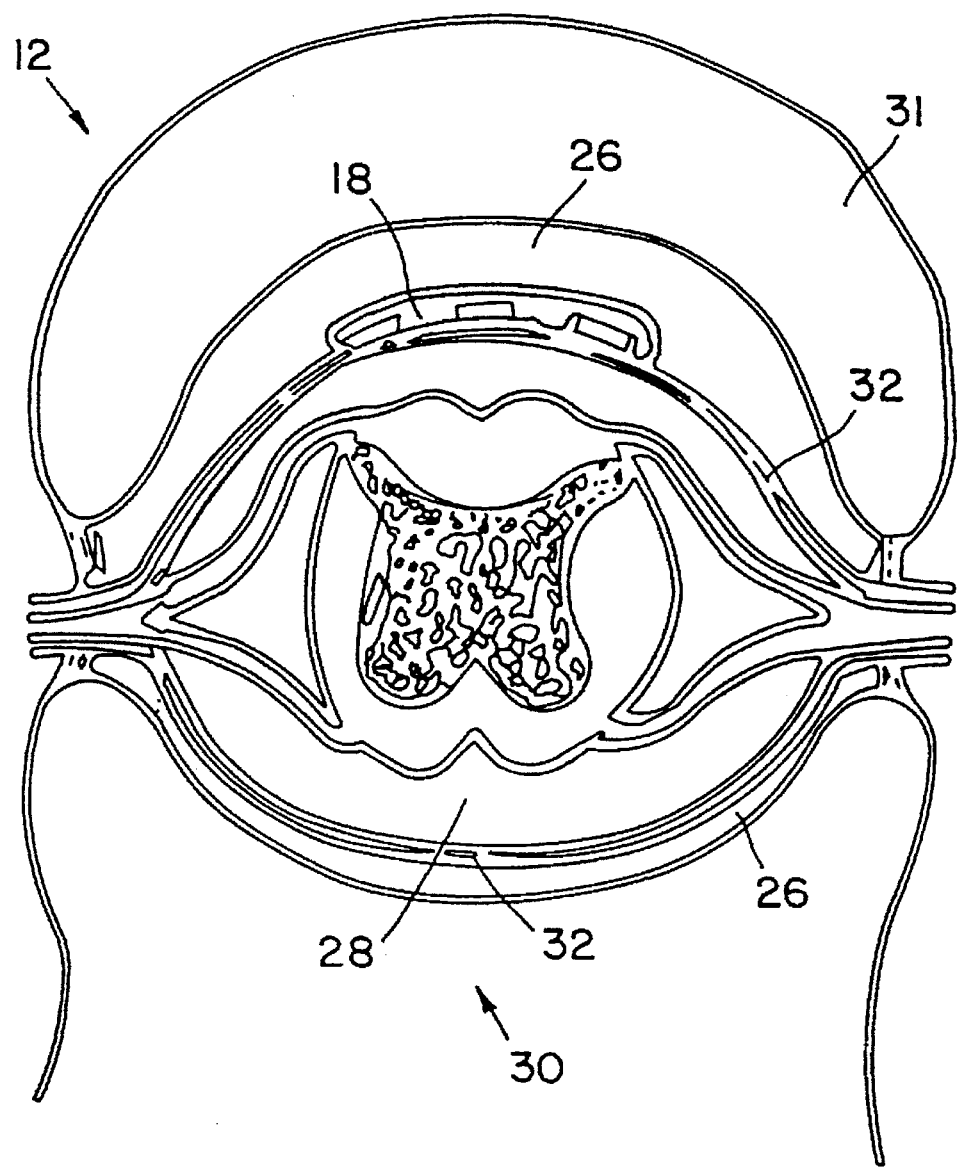
FIG. 2 is a cross sectional view of the spinal cord showing implantation of an insulated lead of the present invention.

FIG. 2 is a cross sectional view of spine 12 showing implantation of the distal end of insulated lead 16 at point 18 within epidural space 26. Also shown is the subdural space 28 filled with cerebrospinal fluid (cfs), vertebral body 30, vertebral arch 31, and dura mater 32.

The following models were developed to compute the effects of multiple superimposed field stimulation of the spinal cord particularly related to the problems of paresthesia coverage and unwanted motor responses. The results obtained show that using multiple field stimulation it is possible to change the paresthesia pattern from symmetrical to asymmetrical or vice versa to correct for changes in paresthesia pattern due to postoperative lead displacement, and also to reduce the activation of dorsal root fibers in favor of dorsal column fibers to reduce the occurrence of motor responses. After the explanation of the models, the invention incorporating the information provided by the models will be described.

Two complementary models provide the theoretical basis for the instant invention. One model is a three dimensional volume conductor model of the spinal cord and its surroundings which incorporates the major macro anatomical structures with the corresponding electrical conductivities and the stimulating electrodes. The second model represents the electrical properties of the largest myelinated dorsal root and dorsal column nerve fibers. These models are extensively described by J. J. Struijk in his Doctor of Philosophy thesis at the University of Twente, the Netherlands "Immediate Effects of Spinal Cord Stimulation", and in four publications in peer review journals (IEEE Trans on Biomed Engin, IEEE Trans on Rehab Engin).

In order to assess the direct effects of stimulation on the nerve fibers a two step procedure was followed. First, the potential field in the volume conductor model was calculated. Second, this field was applied to the nerve fiber model to determine which fibers are excited by the stimulation. The results of these calculations, shown in later figures as isopotential lines and nerve fiber recruitment areas in the dorsal columns of the spinal cord, provide the effects of changing various stimulation parameters.

Figure 3:
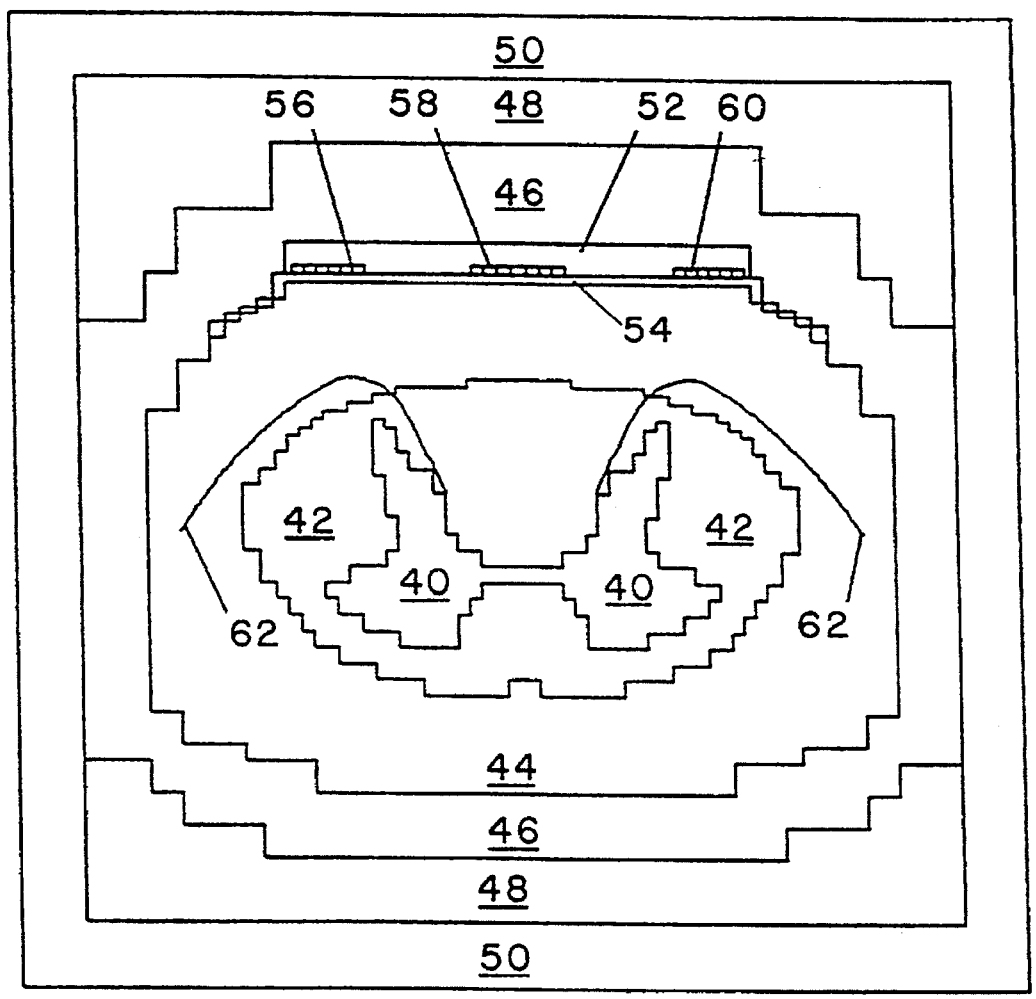
FIG. 3 is a simplified geometric model of the cross section of the midcervical portion of the spinal cord used for computer modeling.

Three dimensional volume conductor models of the spine 12 were developed using a simplified model of a transverse section of the midcervical spinal cord as shown in FIG. 3. A similar model of the midthoracic region was also studied. FIG. 3 shows the spinal cord composed of gray matter 40, white mater 42, cerebrospinal fluid (csf) 44, epidural space 46, vertebral bone 48, surrounding tissues represented by layer 50, and a thin layer of dura mater 54. This figure also shows electrode contact insulation 52 and electrical contacts 56, 58 and 60 for two channel stimulation. The electrodes 56, 58 and 60 are positioned in the dorsal epidural space 46 next to the dura mater 54.

The electrical conductivities for these various elements are given in the following table A. The thickness of the dorsal csf layer was measured from magnetic resonance imaging (MRI) scans obtained from twenty six subjects. In the midcervical and the midthoracic models the average thicknesses of the dorsal csf layers, 2.4 mm and 5.6 mm respectively, were used. This MRI study by Holsheimer et al. appears in Amer J. Neuroradiol.

The three dimensional volume conductor model was made up of discrete elements using a rectangular grid with variable grid spacings. The length of the model was 60 min. The number of grid points was 57 times 57 times 57 which is equal to 185,193. A finite difference method was used to apply the governing Laplace equation to discrete elements. The resulting set of linear equations was solved using a Red-Black Gauss-Seidel iteration with variable overrelaxation.

A fiber model for the dorsal column fibers was based upon D.R. McNeal's "Analysis of a model for excitation of myelinated nerve", IEEE Transactions Biom. Eng., Vol 23, pp. 329–337, 1976. In the model used here collaterals entering the dorsal and ventral horns (grey matter) of the spinal cord model are attached to every second node of Ranvier of a 21-noded fiber. The diameters of these collaterals were one third of the diameter of the corresponding dorsal column fiber which was 10 micrometer. For the dorsal root fibers a cable model with a curved trajectory was used, the proximal end being connected to a dorsal column fiber model. The dorsal root fiber model had a diameter of 10 micrometer. In order to assess the direct effects of stimulation on the nerve fibers, the potential field in the volume conductor model is calculated and then the potential field is applied to the nerve fiber models to determine which fibers are excited by the stimulation.

TABLE A

| CONDUCTIVITIES OF THE VOLUME CONDUCTOR COMPARTMENTS [S/sq. M] | |
| --- | --- |
| grey matter | 0.23 |
| white matter (longitudinal) | 0.60 |
| white matter (transverse) | 0.083 |
| cerebrospinal fluid | 1.70 |
| epidural space | 0.040 |
| dura matter | 0.030 |
| vertebral bone | 0.040 |
| surrounding layer | 0.004 |
| electrode insulation | 0.001 |

These models were used to evaluate the differences between a stimulation field developed by pulses from a single pulse generator and a stimulation field developed by two separate pulse sources. The circuit of FIG. 4A was used for the two sources stimulation model having electrodes 56, 58 and 60 and V1 voltage source 64 and V2 voltage source 66. Electrode 58 has a median position while electrodes 56 and 60 have lateral positions with respect to the spinal cord.

Figure 4A:
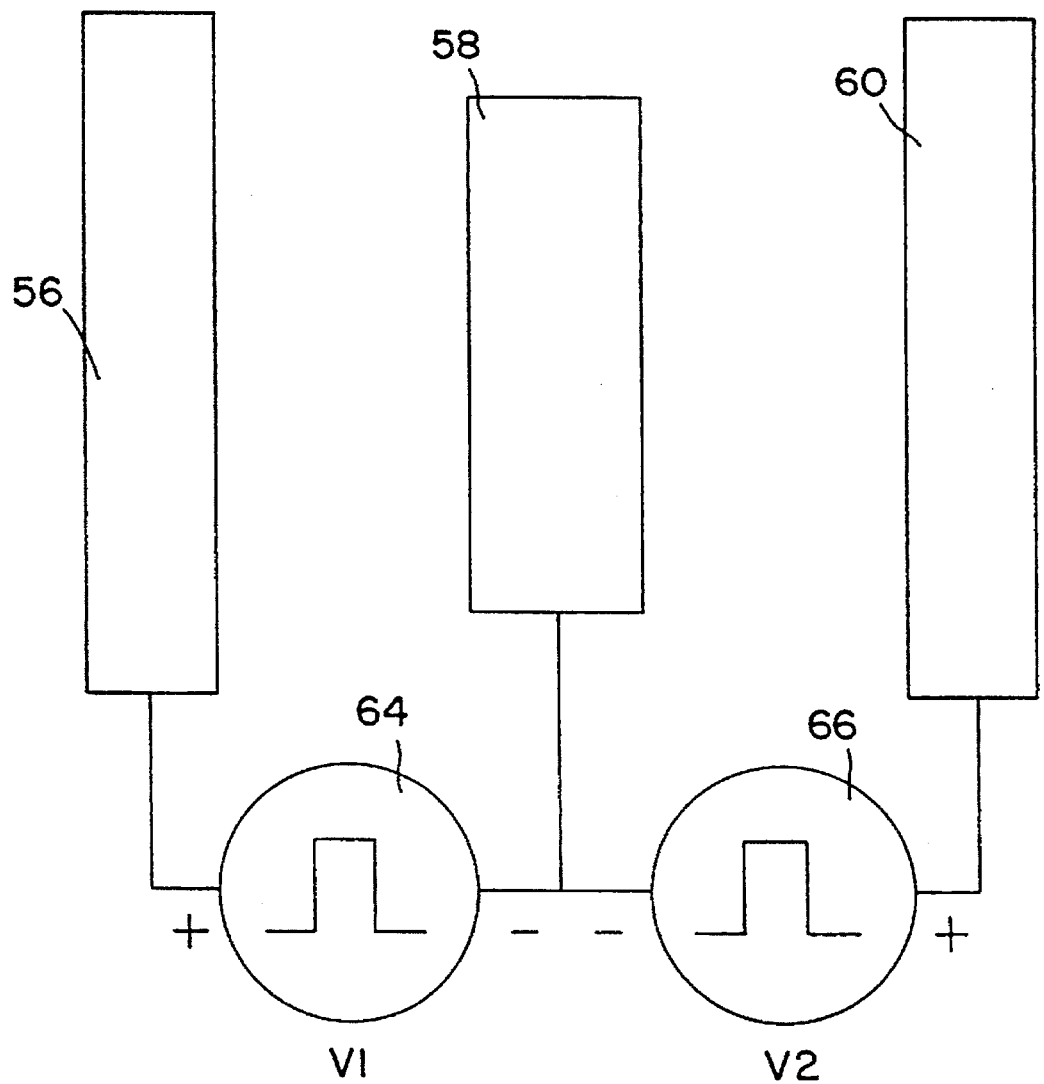
FIG. 4A is a schematic drawing of three in-line electrodes and their connections to two pulse generators.
Figure 4B:
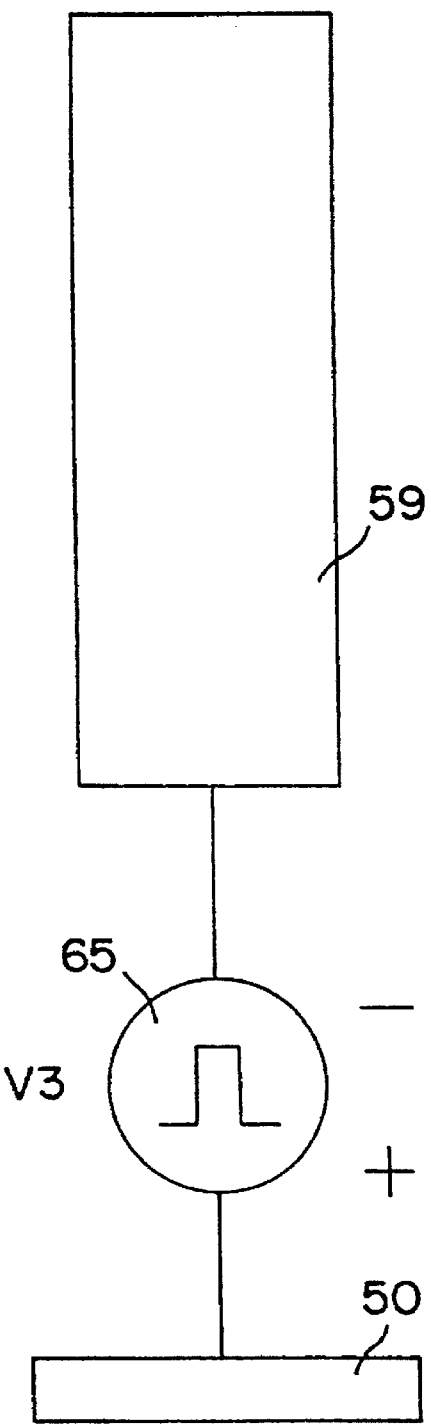
FIG. 4B is a schematic drawing of a stimulating cathodal electrode and a distant anodal electrode and their connections to one pulse generator used in monopolar stimulation.

The circuit of FIG. 4B was used for a single source monopolar stimulation model having voltage source 65 applied between electrode 59 and the outside of layer 50 of the spinal cord model of FIG. 3. The outside of layer 50 is used for the reference connection because the positive anode of V3 from voltage source 65 is assumed to connect to the case of the implantable pulse generator, which is distant from the spinal cord.

The electrode areas used in the models were approximately 12 square millimeters in size because this size has been approved by the United States Federal Drug Administration. The contact separation is larger than the thickness of the dorsal csf layer to reduce the shunting effect of this well conducting layer. The contact separation is on the order of the distance between the dorsal root entry zone and the spinal cord midline. In FIG. 4A, anode contacts 56 and 60 are longer than cathode contact 58. This provides a shielding effect by the outer (anodal) electrodes even if the lead is somewhat rotated in the coronal plane, which is the case if the lead has not been implanted perfectly rostrocaudally. The shielding effect will diminish slightly if the outer anodal electrodes 56 and 60 are shorter than the cathodal electrode 58.

Figure 5:
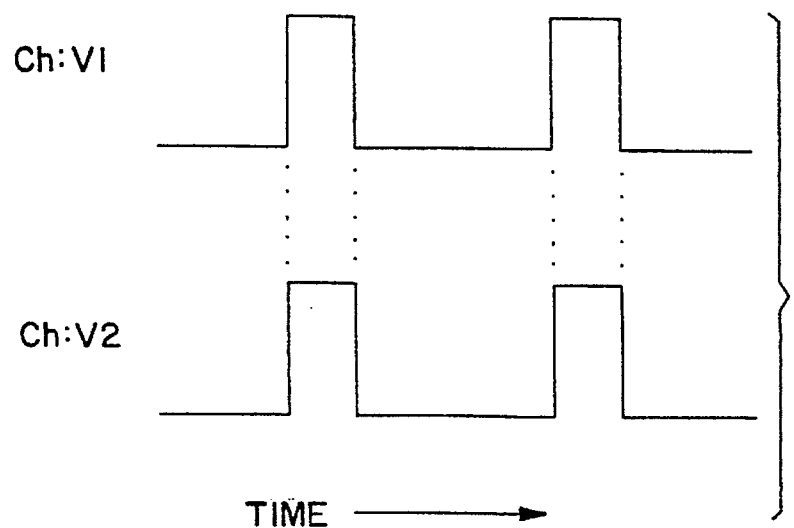
FIG. 5 shows simultaneous pulses from two pulse generators.

V1, V2 and V3 pulses, generated by voltage sources 64, 66 and 65 respectively of FIGS. 4A and 4B, have a pulse width of 210 microseconds. There are two modes of operation for the two voltage sources 64 and 66. Mode one, shown in FIG. 5, has simultaneous outputs of V1 and V2. Mode two, shown in FIG. 6, has the outputs V1 and V2 offset in time. There is also an independent amplitude control of voltage sources 64 and 66 to provide different V1 and V2 amplitudes.

Figure 7:
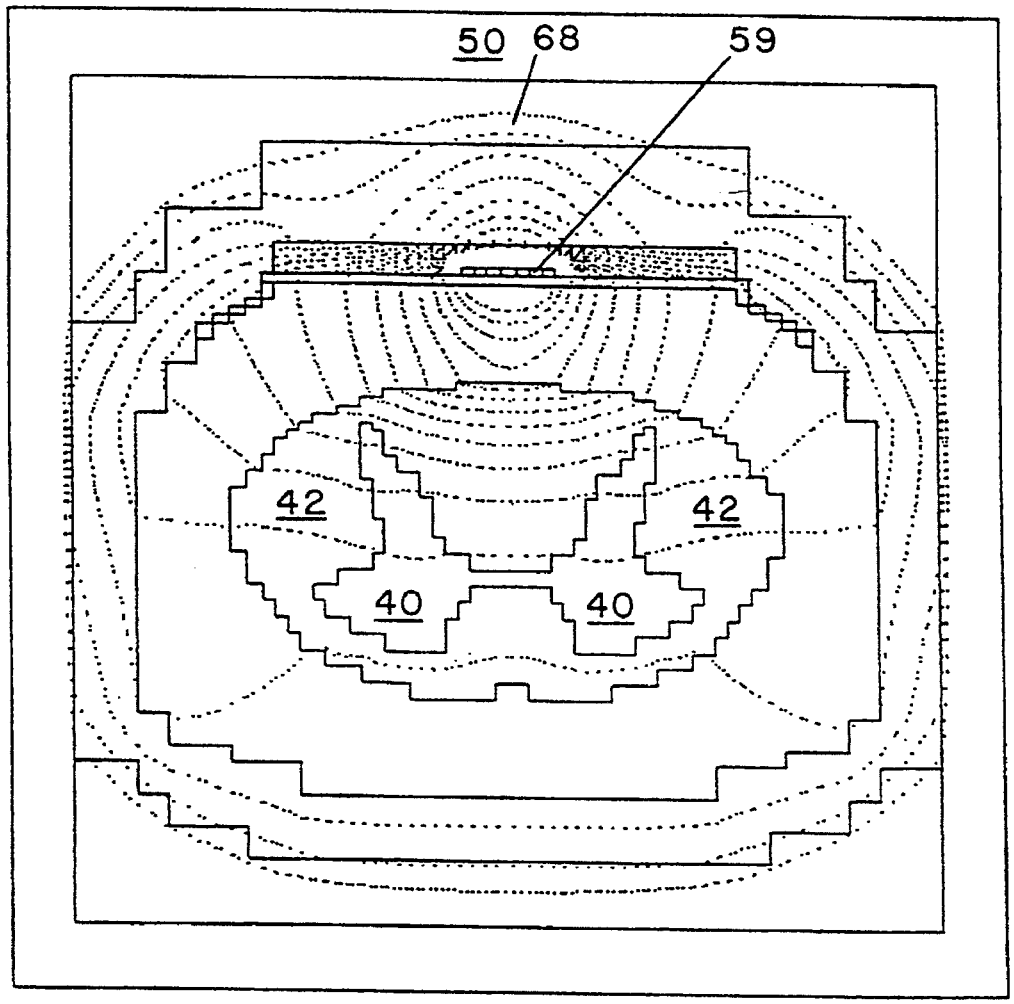
FIG. 7 shows the resulting electrical potential field when a single pulse train of FIG. 5, generated by the circuit of FIG. 4B, is applied to the model, with the field being represented by isopotential lines.
Figure 8:
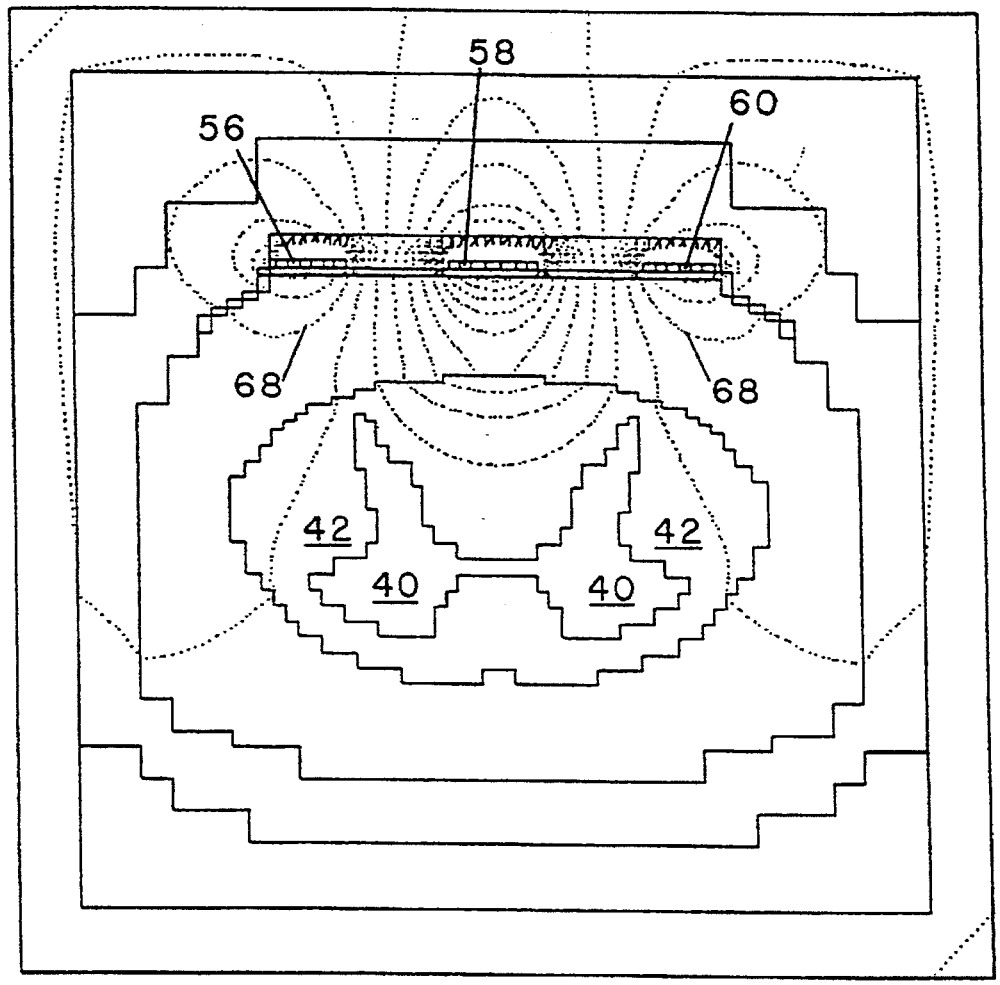
FIG. 8 shows the resulting potential field when two simultaneous pulse trains of equal amplitude, generated by the circuit of FIG. 4A, are applied to the model.
Figure 9:
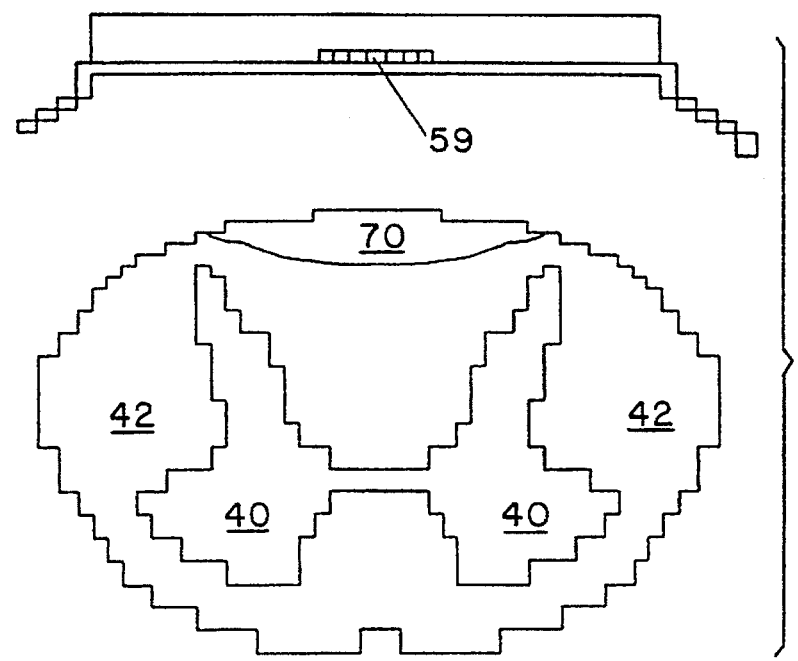
FIG. 9 shows the recruited area related to the potential field shown in FIG. 7 using the single pulse train circuit of FIG. 4B.
Figure 10:
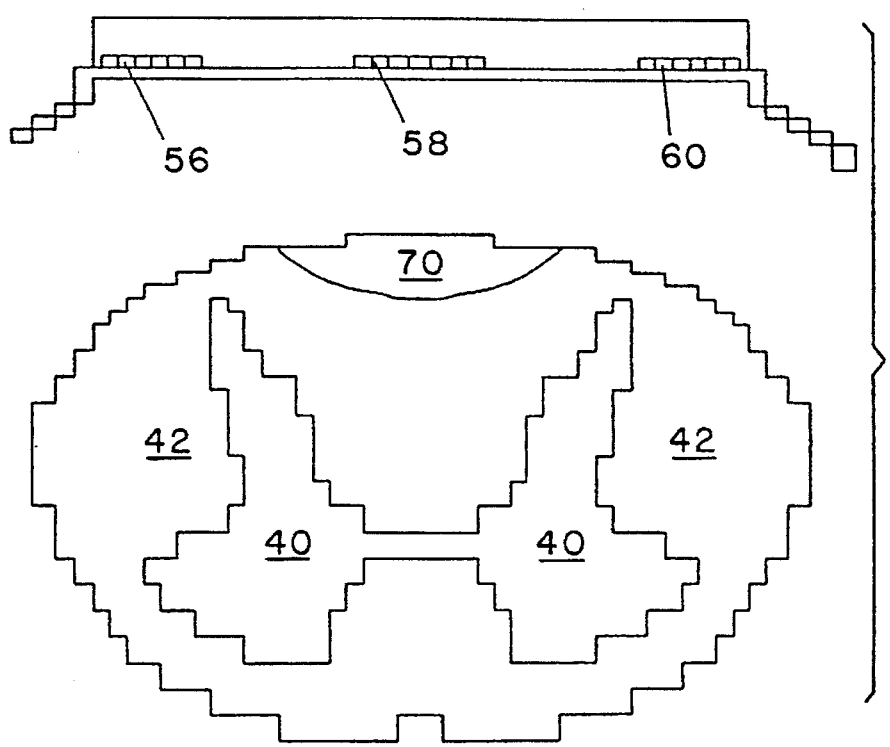
FIG. 10 shows the recruited area related to the potential field of FIG. 8 with two simultaneous pulse trains of equal amplitude when using the circuit of FIG. 4A.

FIG. 7 shows the resulting potential field represented by isopotential lines 68 when the pulse is applied to the model by a single cathode 59 and a distant anode 50 as shown in Fig. 4B. FIG. 8 shows the resulting isopotential lines 68 when two pulses with equal amplitudes are simultaneously applied to the model, according to the scheme of FIG. 4A. FIG. 9 shows the resulting recruited area 70 of dorsal column fibers with a diameter of 10 micrometer when a single cathode 59 is used with the same model as that used in FIG. 7. FIG. 10 shows the recruited area 70 for two simultaneous pulses of equal amplitude using the same model as in FIG. 8. These figures show that for stimulation with a transversely positioned tripole the negative potentials and the recruited area of dorsal column fibers are more restricted to the medial part of the dorsal columns than in monopolar stimulation.

The shape of the recruited area of dorsal column fibers does not differ significantly when mono-, bi-, tri-, or quadripolar stimulation with a conventional longitudinal SCS electrode array is given, as was shown by Holsheimer et al. using the same type of model (Stereotact Funct Neurosurg 1991, Vol. 56, pp. 220–233). Calculations also showed that dorsal root fibers need higher voltages for their activation when stimulating with a transversely positioned tripole, which will reduce the probability of motor responses significantly.

Figure 11:
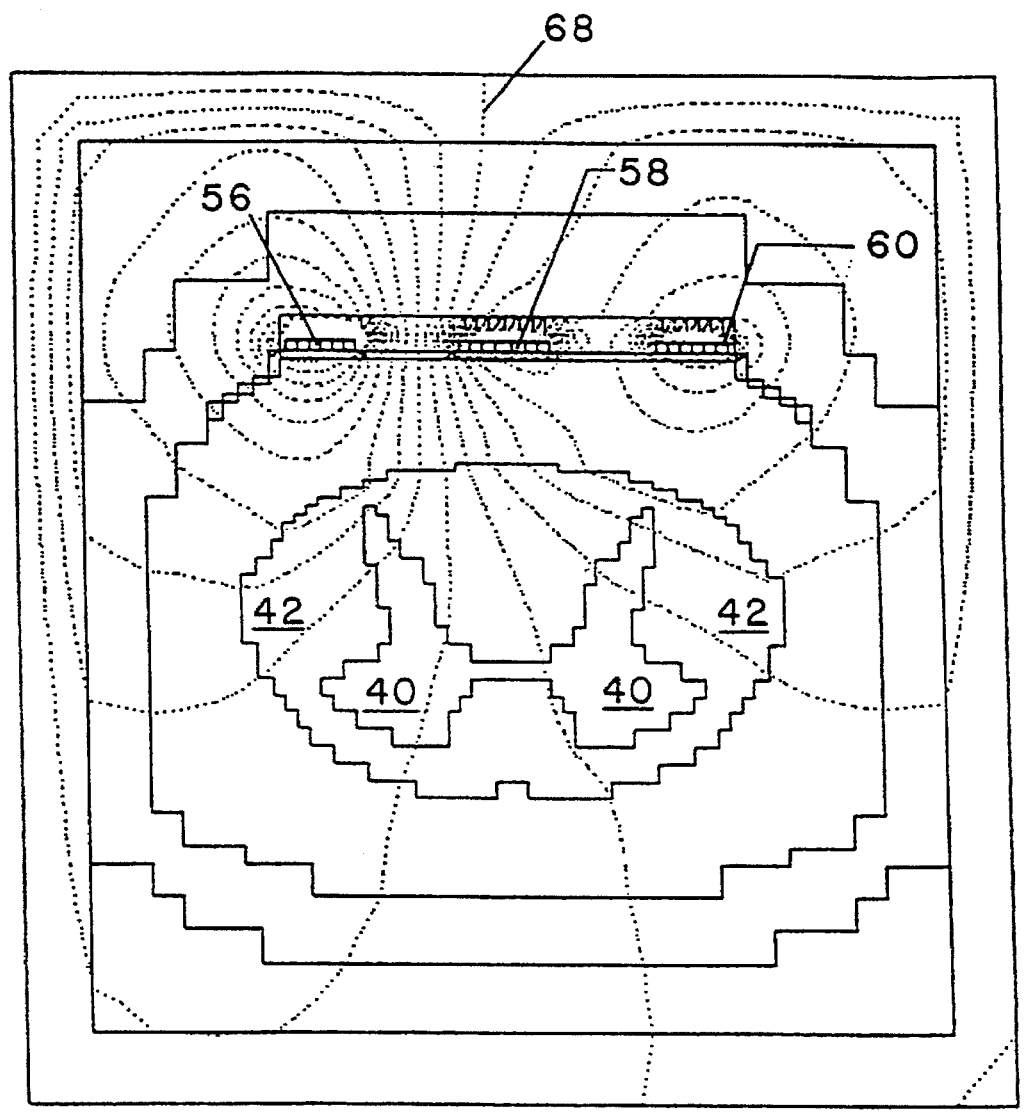
FIG. 11 shows the resulting potential field when the amplitude of the pulse train, generated by V2 of FIG. 4A, is set equal to zero, with electrodes 58 and 60 having the same negative voltage and both acting as cathodes.
Figure 12:
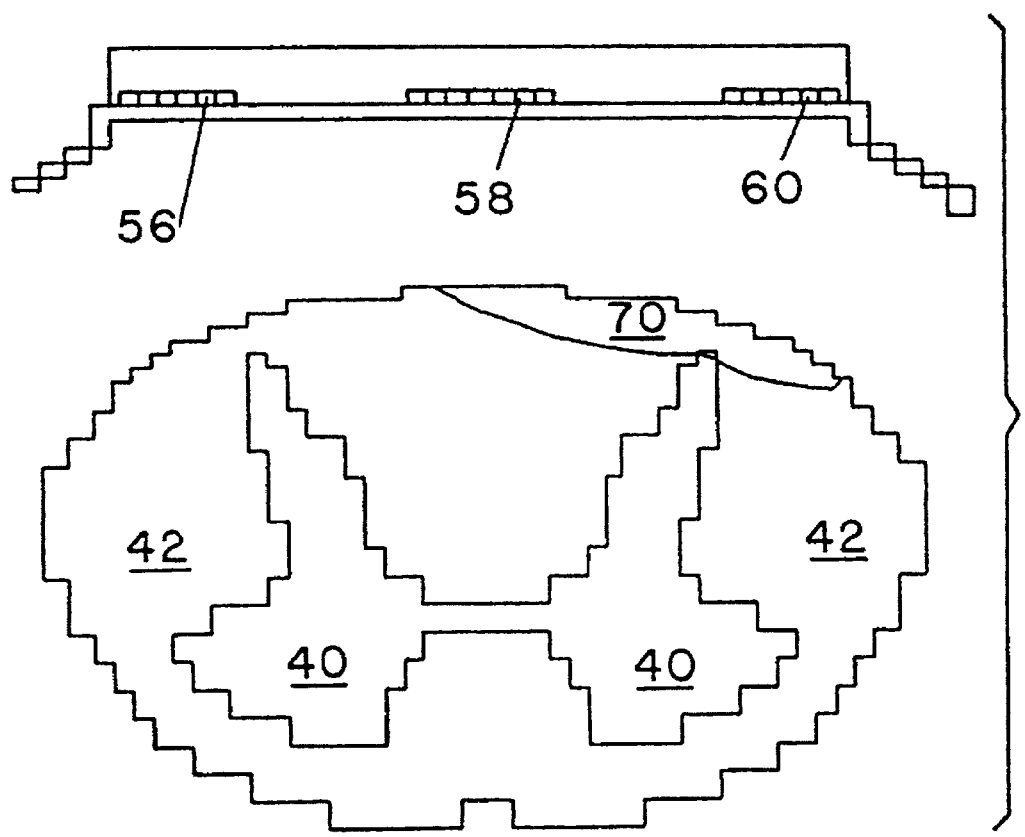
FIG. 12 shows the recruited area related to the potential field of FIG. 11, with the pulse train generated between electrodes 58 and 60 having a zero amplitude such that the electrodes have the same negative voltage.

The use of simultaneous pulses from two unbalanced sources results in a controllable asymmetrical stimulation which is impossible to attain with single source stimulation. The resulting isopotential lines 68 obtained when V2 of FIG. 4A is set equal to zero, with electrodes 58 and 60 having the same potential, and applied to the model is shown in FIG. 11. This shows how to obtain asymmetrical stimulation by merely using unbalanced sources with multiple electrodes in a transverse plane, even though the electrode positions are perfectly symmetrical. FIG. 12 shows that a large shift in the recruited area 70 of dorsal column fibers is also obtained using these unbalanced sources. The example shown here is the most extreme one with V2 equal to zero volts.

Figure 13:
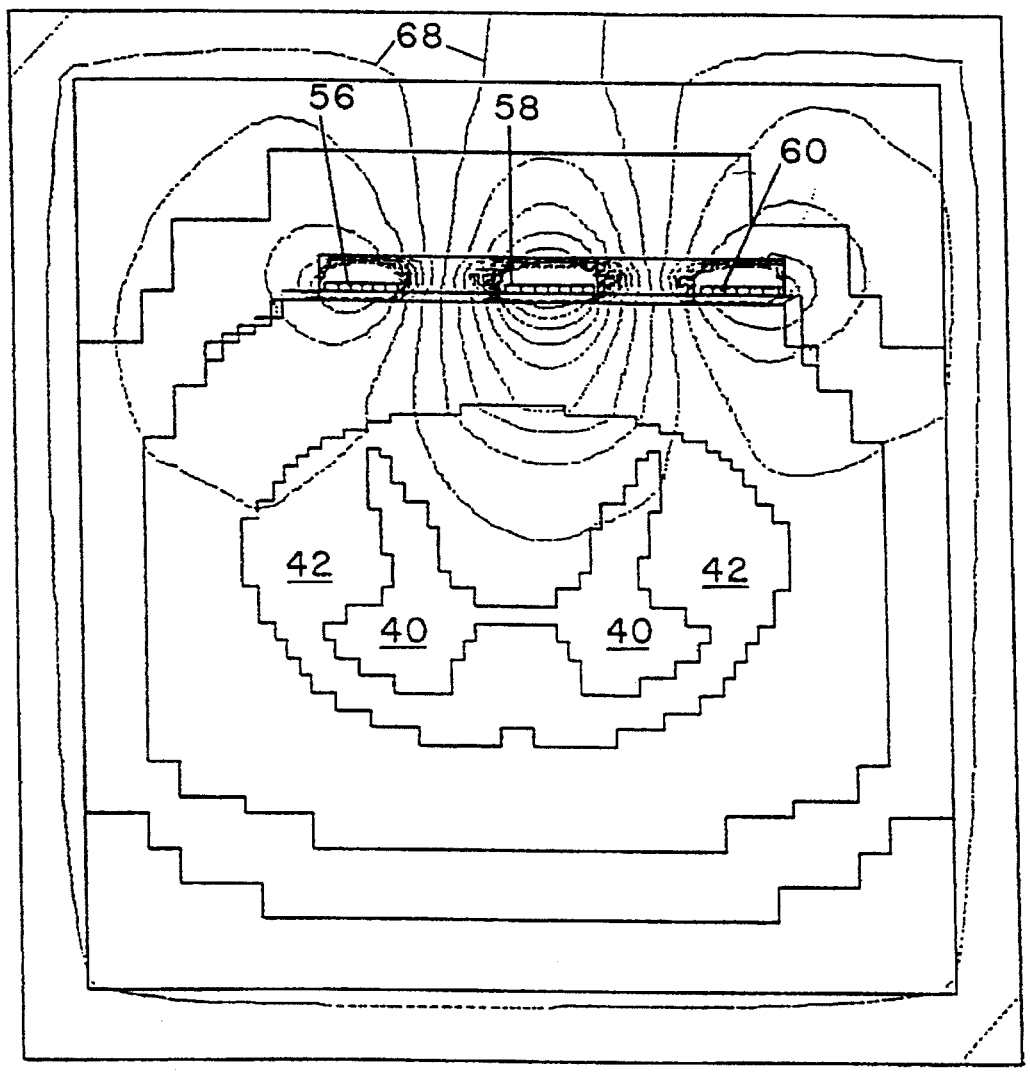
FIG. 13 shows the resulting potential field when two simultaneous pulse trains of equal amplitude are applied to the model with the center electrode offset 1.0 mm. from the spinal cord midline.
Figure 14:
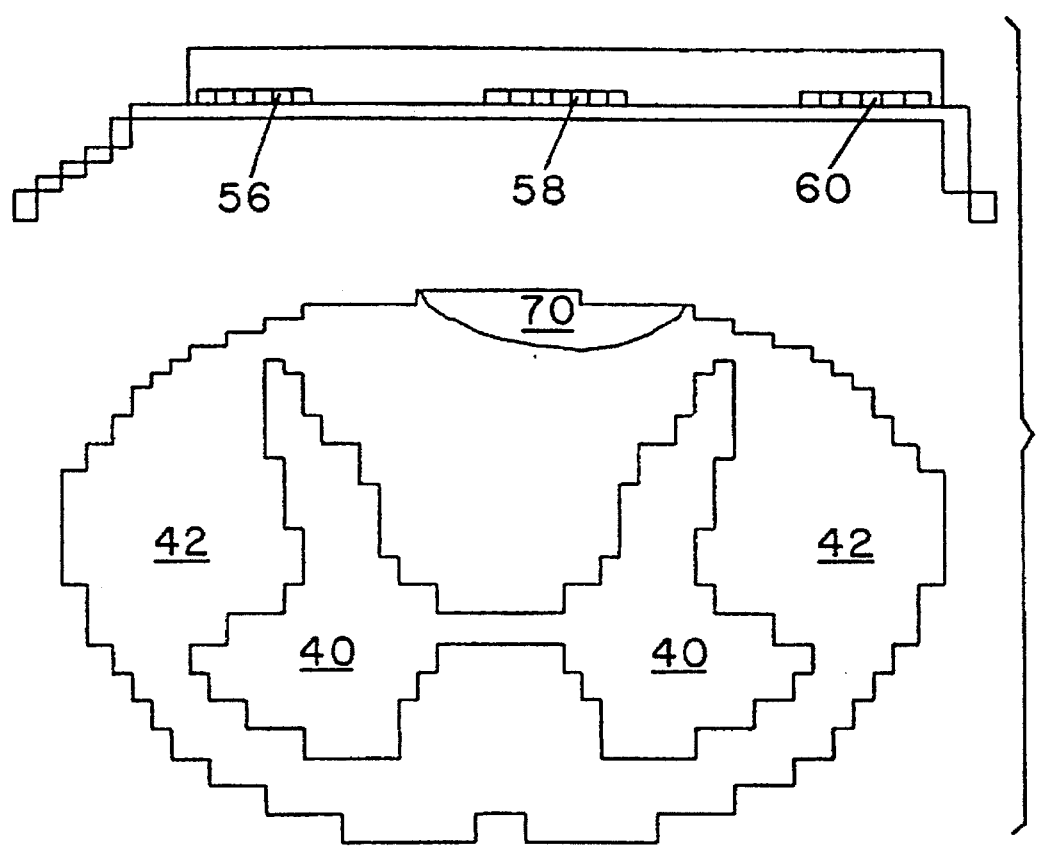
FIG. 14 shows the recruited area related to the potential field of FIG. 13 having two simultaneous pulse trains with the same amplitude and with the center electrode offset 1.0 mm from the spinal cord midline.

If the lead is not at the spinal midline due to lead migration, by lateral positioning during surgery, or to an asymmetrical position of the spinal cord in the spinal canal, it is still possible to obtain an almost symmetrical stimulation. FIG. 13 shows the resulting isopotential lines 68 and FIG. 14 shows recruited area 70 for an electrode offset of 1.0 mm from midline with V1 and V2 pulses simultaneous and of equal amplitude. The recruited area is asymmetrical even though the voltage sources are equal.

Figure 15:
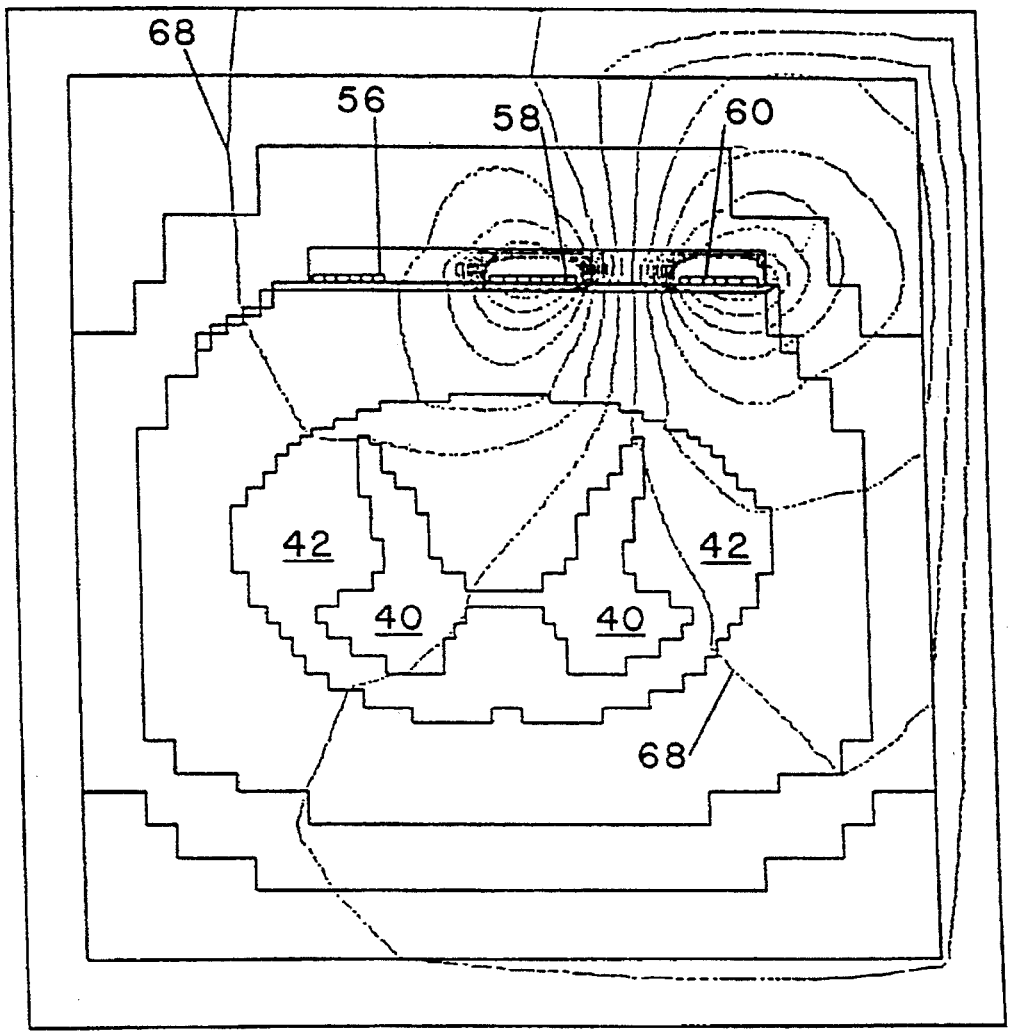
FIG. 15 shows the resulting potential field when two simultaneous pulse trains are applied to the model with the pulse amplitude between electrodes 56 and 58, V1, lower than the pulse amplitude between electrodes 58 and 60, V2, and the center electrode being offset 1.0 mm from the spinal cord midline.
Figure 16:
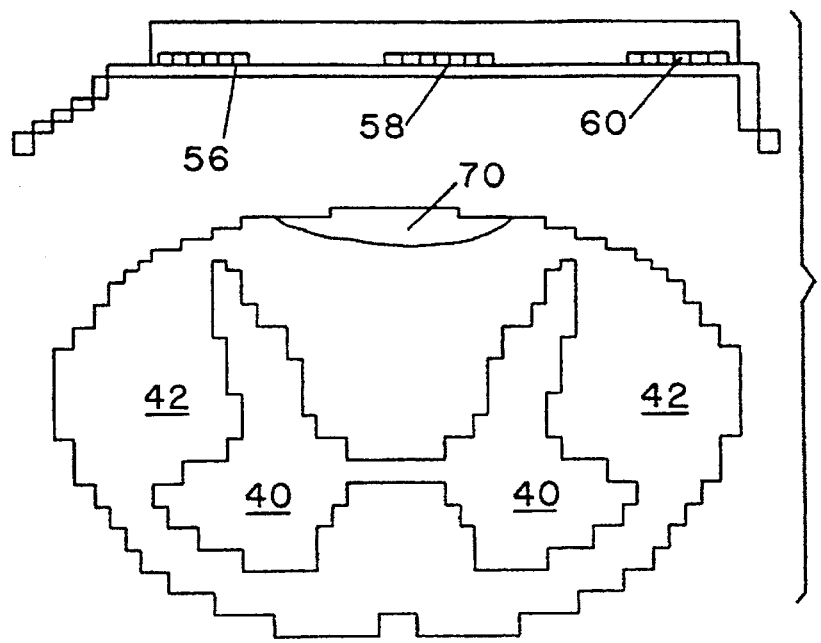
FIG. 16 shows the recruited area related to the potential field of FIG. 15 having two simultaneous pulse trains with different amplitudes, and with the center electrode offset 1.0 mm from midline of the spinal cord.

FIGS. 15 and 16 show the results with an electrode offset of 1.0 mm from midline and simultaneous inputs V1 and V2 of FIG. 4A set equal to 2.26 volts and 4.52 volts respectively to obtain an asymmetrical field. These figures show that the shape of potential field and recruited area are modified by this unbalanced input, resulting in an almost symmetrical recruited area 70 in the dorsal columns in FIG. 16.

Figure 6:
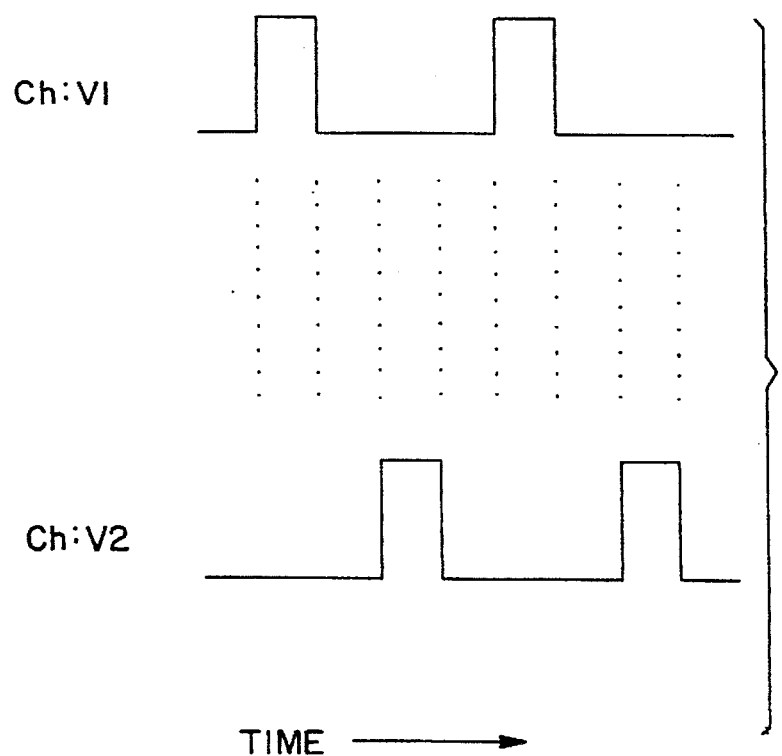
FIG. 6 shows alternating pulses from two pulse generators.
Figure 17:
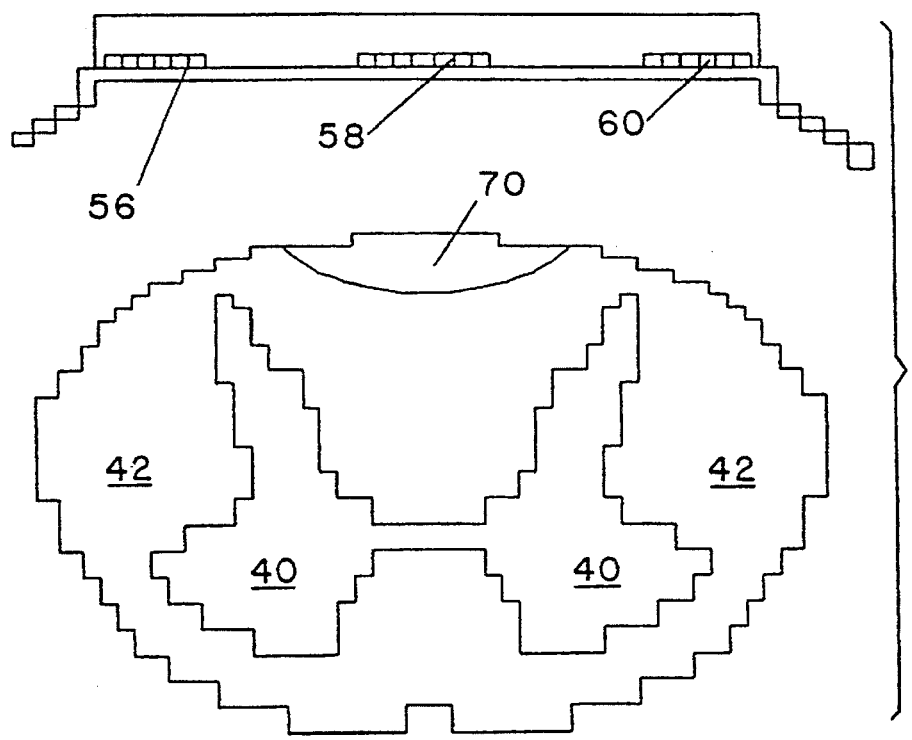
FIG. 17 shows the recruited area when two simultaneous pulse trains of equal amplitude are applied to the model, with the center electrode centered at the spinal cord midline.
Figure 18:
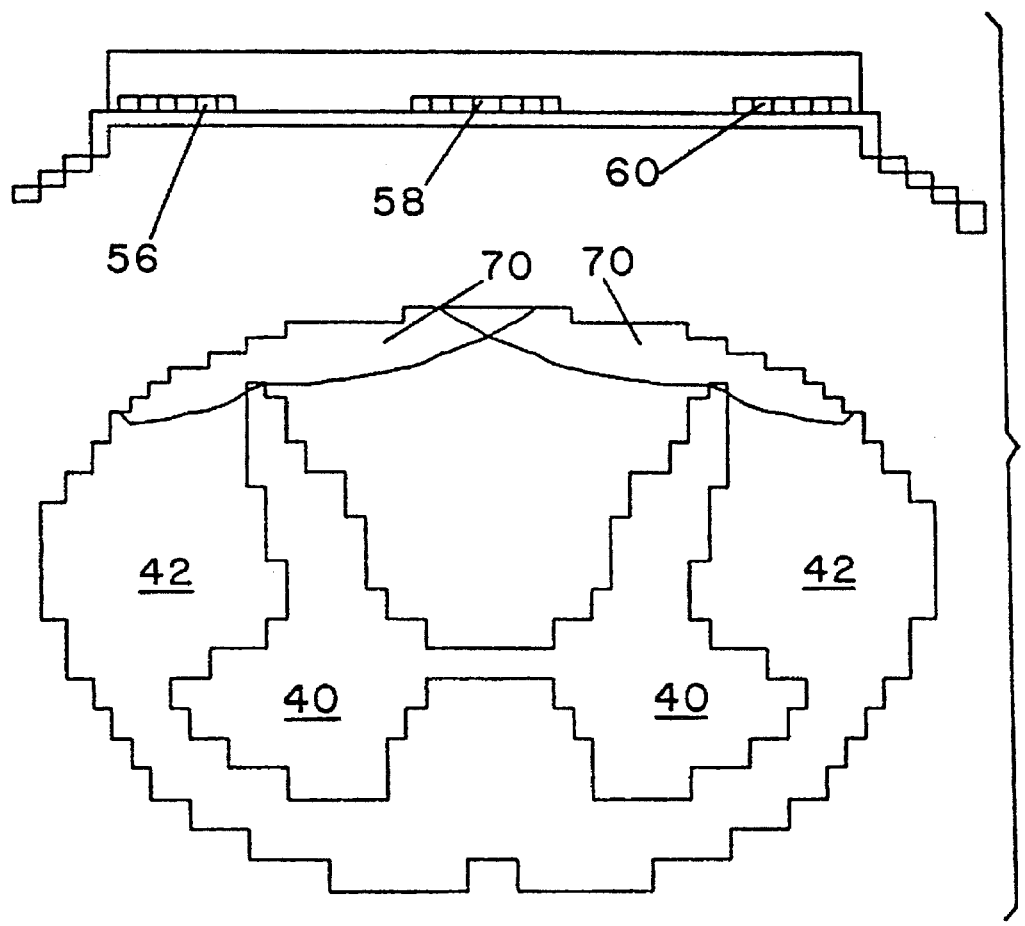
FIG. 18 shows the recruited area when the alternating pulse trains of equal amplitude from FIG. 6 are applied to the model.

FIG. 17 shows the recruited area 70 for equal amplitude simultaneous pulses applied to the model by a symmetrically positioned transverse electrode array, and FIG. 18 shows the recruited areas 70 for equal amplitude offset pulses of FIG. 6 applied to the model, which is the union of two asymmetrical recruited areas.

When a pulse $V_1$ is applied to the symmetrically positioned transverse electrode array, the area labeled 70a in FIG. 18 is recruited. Likewise, when a pulse $V_2$ is applied to the electrode array, the area labeled 70b in FIG. 18 is recruited. When the amplitude of pulses $V_1$ and $V_2$ are sufficiently high, an area of overlap of the recruited areas 70a, b occurs. This area of overlap is labeled 70c in FIG. 18.

Since the pulses $V_1$ and $V_2$ that cause areas 70a,b to be recruited are offset from each other, areas 70a and 70b will be recruited at corresponding intervals offset from each other. Area 70c will be recruited when either area 70a or 70b is recruited. As a result, area 70c will be recruited at a rate greater than the rate of recruitment for areas 70a and 70b.

For example, if pulses $V_1$ and $V_2$ are offset pulses each having a frequency of 50 Hz., areas 70a and 70b will be recruited at a frequency of 50 Hz. Area 70c, however, will be recruited when ever either area 70a or 70b is recruited. Consequently, area 70c will be recruited at a frequency of 100 Hz.

The results of this modeling indicate that areas of recruited spinal nerve fibers can be modified, when using more than one source for stimulation of the spinal cord versus single source stimulation, in that a variety of parameters can now be changed to vary the stimulated area and intensity. These parameter changes can obviously be extended. For example, the effects of only two sources were investigated here, but these same parameters can also be changed if three, four or more independent sources were employed with analogous results.

The information developed using these models has been incorporated into this invention in two embodiments. FIG. 19 shows pulse generator 14 with positive going pulse outputs 72, 74, 76, and 78 with respect to ground reference 80. The outputs at 72, 74, 76, and 78 are each selectable in time as were V1 or V2 of FIG. 6, and each output can be changed in amplitude independent of the other outputs or can be electrically disconnected. Line 16 has electrodes 38 connected to these outputs with wire 80A connecting output 72 to electrode 38A, wire 80B connecting output 74 to electrode 38B, wire 80C connecting output 76 to electrode 38D, wire 80D connecting output 78 to electrode 38E, and wire 80E connecting ground reference 80 to electrode 38C. Electrodes 38 have different sizes with electrodes 38A, 38B, 38D and 38E, which are connected to the voltage outputs of pulse generator 14, wider than interspersed electrode 38C which is connected to ground reference 80. This provides the Improved shielding effect described previously.

With these connections and with the time and amplitude variables of pulse generator 14 a stimulation field will be set up between each electrode connected to a pulse generator output and the interleaved electrode connected to the pulse generator ground reference. The two modes of stimulation, shown in FIGS. 5 and 6, used in the modeling study are obtained by connecting pulse generator 14 to electrodes 38 as described above. If a smaller number of electrodes are used the unused outputs of pulse generator 14 are electrically disconnected.

FIG. 20 shows a second embodiment with pulse generator 14 having additional outputs with the same characteristics regarding the outputs, ground reference and capabilities as before, and with lead 17 having electrodes 39.

In this second embodiment lead 17 has electrodes 39 connected to the outputs of pulse generator 14 differently, with wire 80A connecting output 72 to electrode 39A, wire 80B connecting output 74 to electrode 39C, wire 80C connecting output 76 to electrode 39D, wire 80D connecting output 78 to electrode 39F, wire 80G connecting output 82 to electrode 39G, and wire 80H connecting output 84 to electrode 39I. Wire 80E connecting electrode 39B to ground reference 80, wire 80F connecting electrode 39E to ground reference 80, and wire 80I connecting electrode 39H to ground reference 80, establish the ground connections. Electrode 39B is centered between the driven electrodes 39A and 39C. Similarly, the ground referenced electrode 39E is centered between the driven electrodes 39D and 39F, and electrode 39H is centered between electrodes 39G and 39I.

With this second embodiment, the stimulation can be applied at different spinal levels by using one out of three combinations 39A, B, and C; 39D, E, and F; or 39G, H, and I. Again, the unused outputs of pulse generator 14 are electrically disconnected.

This system provides the capability to change the depth and location of the stimulation by changing the amplitude or timing of one field with respect to another. The modeling of the fields described earlier shows that results are changed markedly by the use of multiple pulse generators connected to different electrodes positioned in a transverse plane with respect to the spinal cord.

While this invention has been described with reference to illustrative embodiments, this description is not intended to be constructed in a limiting sense. Various modifications of the illustrative embodiments, as well as other embodiments of the invention, will be apparent to persons skilled in the art upon reference to this description. It is therefore contemplated that the appended claims will cover any such modifications or embodiments as fall within the true scope of the invention.

We claim:

1. An apparatus for stimulating neural tissue in a spinal column comprising:

a) a source of electrical pulses having a plurality of channels through which electrical pulses produced by the source of electrical pulses are passed, the source of electrical pulses producing output pulses in each of the channels, the source of electrical pulses having means for independently changing parameters of the output pulses in each channel;

b) a lead adapted to be implanted near the spinal column, the lead connected to the source of electrical pulses, the lead having a proximal and a distal end and a first axis extending parallel to the spinal column when the lead is implanted near the spinal column, the lead having at least a first, a second and a third electrode located substantially in line near the distal end of the lead, the first, second and third electrodes located generally along a second axis that is generally perpendicular to the first axis of the lead, the lead having at least the first and third electrodes each connected to a different channel of the source of electrical pulses and the second electrode being generally centered with respect to the first and third electrodes and also being a common cathode with respect to the first and third electrodes so that cathode/anode pairs are formed between each of the first and second electrodes and the second and third electrodes, respectively, the source of electrical pulses producing pulses delivered through the channels to at least the respective first and third electrodes, the pulses through the channels to the respective first and third electrodes not overlapping in time during any portion of each pulse.

2. Apparatus as in claim 1 wherein the source of electrical pulses has means for independently changing timing of the production of each output pulse of each channel with respect to the production of each output pulse of other channels.

3. Apparatus as in claim 1 wherein at least one of the electrodes is generally planar having a first dimension perpendicular to the first axis of the lead and having a second dimension parallel to the first axis of the lead.

4. An apparatus for stimulating neural tissue in a spinal column, the spinal column having a dorsal column, the dorsal column having dorsal root entry zones, the apparatus comprising:

a) a source of electrical pulses having a plurality of channels, the source of electrical pulses producing output pulses in each of the channels, the source of electrical pulses having means for independently changing parameters of the output pulses in each channel;

b) an implantable lead adapted to be implanted near the spinal column, the lead connected to the source of electrical pulses, the lead having a proximal and a distal end, an outer surface and a first axis extending parallel to the direction of elongation of the spinal column when the lead is implanted near the spinal column, the lead having at least three electrodes near the distal end of the lead extending along the outer surface of the lead along a second axis that is generally perpendicular to the first axis of the lead, the lead having a first class of electrodes located along two sides of the first axis of the lead and a second class of electrodes located generally along the first axis of the lead, each electrode of the first class of electrodes being an anode and connected to a different channel output of the source of electrical pulses, and each electrode of the second class of electrodes being a cathode and connected to the common voltage reference of the source of electrical pulses, the source of electrical pulses producing pulses in the first class of electrodes that do not overlap in time during any portion of each pulse.

5. Apparatus as in claim 4 wherein the source of electrical pulses has means for independently changing the timing of the output pulse of a channel with respect to the other channels.

6. Apparatus as in claim 4 wherein the outer surface of the electrodes is planar having a first dimension perpendicular to the first axis of the lead and having a second dimension parallel to the first axis of the lead.

7. Apparatus as in claim 6 wherein the first class of electrodes has a predetermined second dimension and wherein the second class of electrodes have a smaller second dimension than the second dimension of the first class of electrodes.

8. Apparatus as in claim 7 wherein the second class of electrodes has a larger first dimension than the first dimension of the first class of electrodes.

9. Apparatus as in claim 4 wherein the source of electrical pulses has means for electrically disconnecting any output channel from a connected electrode.

10. Apparatus as in claim 4 wherein the source of electrical pulses has means for electrically disconnecting any channel and the common voltage reference from a connected electrode.

11. Apparatus as in claim 4 wherein the electrodes connected to a channel output of the source of electrical pulses are spaced apart by a distance about equal to the distance of separation of the dorsal root entry zones of the spinal column near where the lead is implanted.

12. Apparatus as in claim 4 wherein the electrodes in the first class of electrodes are spaced apart by a distance about equal to the separation of the dorsal root entry zones of the spinal column near where the lead is implanted.

13. A system for causing excitation in nerve fibers of a spinal column or other neural tissue of a spinal cord, the spinal column having epidural and intrathecal space and dura, the spinal column having a dorsal column, the dorsal column having dorsal root entry zones, the system comprising:

a. an electrode array comprising a first, a second and a third electrode, the second and third electrodes located on either side of the first electrode, the first electrode being a cathode, the second and third electrodes each being an anode so that cathode/anode pairs are formed between the first and second and first and third electrodes, respectively, each electrode adapted to be placed in the epidural or intrathecal space of the spinal column;

b. a source of electrical pulses connected to and sending pulses to the cathode/anode pairs formed between the first and second electrodes and the first and third electrodes, respectively, the pulses sent to the cathode/anode pairs not overlapping in time for any portion of each pulse;

whereby, an electric field of variable strength and location is generated in the neural tissue and, whereby an electric field having a frequency of double the frequency of the pulses sent to each cathode/anode pair is produced in any area of overlap of the electric fields produced by sending pulses to the cathode/anode pairs.

14. The system of claim 13 wherein the source of electrical pulses produces pulses of variable amplitude and the source of electrical pulses sends electrical pulses of variable amplitude to the electrodes.

15. The system of claim 13 wherein the source of electrical pulses produces pulses of variable pulse width and the source of electrical pulses sends electrical pulses of variable pulse width to the electrodes.

16. The system of claim 13 wherein the second and third electrodes are spaced apart by a distance about equal to the separation of the dorsal root entry zones of the spinal column near where the electrode array is placed.

17. The system of claim 13 wherein the pulse width of each of the pulses produced by the source of electrical pulses is identical.

18. The system of claim 13 wherein the amplitude of each of the pulses produced by the source of electrical pulses is identical.

19. The system of claim 13 wherein the electrode array has a generally planar configuration.

20. The system of claim 13 wherein the electrode array substantially conforms to the dura of the spinal column where the electrode array is placed.

21. A system for causing excitation in nerve fibers of a spinal column or other neural tissue of a spinal cord, the spinal column having a dorsal column, the dorsal column having dorsal root entry zones, the spinal column having epidural and intrathecal spaces and dura, the system comprising:

a. an electrode array comprising at least a first, a second and a third electrode, the second and third electrodes located on either side of the first electrode, the first electrode being a cathode, the second and third electrodes each being an anode so that cathode/anode pairs are formed between the first and second and first and third electrodes, respectively, each electrode adapted to be placed in the epidural or intrathecal space of the spinal column, the second and third electrodes being spaced apart by a distance about equal to the separation of the dorsal root entry zones of the spinal column near where the electrode array is placed, the first, second and third electrodes being located generally along a common axis;

b. a source of electrical pulses connected to and sending pulses to the electrodes so that cathode/anode pairs formed between the first and second electrodes and the first and third electrodes, respectively, the pulses sent to the cathode/anode pairs not overlapping in time for any portion of each pulse, the source of electrical pulses sending electrical pulses of variable parameters to the electrodes;

whereby, an electric field of variable strength and location is generated in the neural tissue and whereby an electric field having a frequency of double the frequency of the pulses sent to each cathode/anode pair is produced in any area of overlap of the electric fields produced by sending pulses to the cathode/anode pairs.

22. The system of claim 21 wherein the source of electrical pulses produces pulses of variable amplitude and the source of electrical pulses sends electrical pulses of variable amplitude to the electrodes.

23. The system of claim 21 wherein the source of electrical pulses produces pulses of variable pulse width and the source of electrical pulses sends electrical pulses of variable pulse width to the electrodes.

24. The system of claim 21 wherein the electrode array substantially conforms to the dura of the spinal column where the electrode array is placed.

25. A system for causing excitation in nerve fibers of a spinal column or other neural tissue of a spinal cord, the spinal column having a dorsal column, the dorsal column having dorsal root entry zones, the spinal column having epidural and intrathecal spaces and dura, the system comprising:

a. an electrode array comprising at least a first, a second and a third electrode, the second and third electrodes located on either side of the first electrode, the first electrode being a cathode and the second and third electrodes each being an anode so that cathode/anode pairs are formed between the first and second and first and third electrodes, respectively, each electrode adapted to be placed in the epidural or intrathecal space of the spinal column;

b. a source of electrical pulses connected to and sending pulses to the second and third electrodes, the source of electrical pulses producing and sending electrical pulses of variable parameters, the pulses sent to the second and third electrodes by the source of electrical pulses not overlapping in time for any portion of each pulse;

c. a common voltage reference connected to the first electrode;

whereby, an electric field of variable strength and location is generated in the neural tissue and whereby an electric field having a frequency of double the frequency of the pulses sent to each cathode/anode pair is produced in any area of overlap of the electric fields produced by sending pulses to the cathode/anode pairs.

26. The system of claim 25 wherein the source of electrical pulses produces pulses of variable amplitude and the source of electrical pulses sends electrical pulses of variable amplitude to the second and third electrodes.

27. The system of claim 25 wherein the source of electrical pulses produces pulses of variable pulse width and the source of electrical pulses sends electrical pulses of variable pulse width to the second and third electrodes.

28. The system of claim 25 wherein the electrode array substantially conforms to the dura of the spinal column where the electrode array is placed.

29. A system for creating and controlling electric fields in neural tissue comprising:

a. an electrode array comprising at least a first, a second and a third electrode, the second and third electrodes located on either side of the first electrode, the first electrode being a cathode and the second and third electrodes each being an anode so that cathode/anode pairs are formed between the first and second and first and third electrodes, respectively, the electrodes adapted to be placed near the neural tissue at an optimal distance from the neural tissue;

b. a source of electrical pulses having at least two channels, each channel producing and sending pulses to the second and third electrodes, the source of electrical pulses producing electrical pulses of variable parameters in each channel, the pulses sent to the second and third electrodes by the source of electrical pulses not overlapping in time for any portion of each pulse;

c. a common voltage reference connected to the first electrode;

whereby, an electric field of variable strength and location is generated in the neural tissue and whereby an electric field having a frequency of double the frequency of the pulses sent to each cathode/anode pair is produced in any area of overlap of the electric fields produced by sending pulses to the cathode/anode pairs.

30. The system of claim 29 wherein the source of electrical pulses produces pulses of variable amplitude and the source of electrical pulses sends electrical pulses of variable amplitude to the second and third electrodes.

31. The system of claim 29 wherein the source of electrical pulses produces pulses of variable pulse width and the source of electrical pulses sends electrical pulses of variable pulse width to the second and third electrodes.

32. A method of controlling a volume of neural tissue stimulation in a spinal column or other neural tissue of a spinal cord, the spinal column having epidural and intrathecal spaces and a dorsal column, the dorsal column having dorsal root entry zones, the spinal column having a midline, the method comprising the steps of:

a. placing a first electrode being a cathode near the midline of the spinal column near the neural tissue to be stimulated at an optimal distance from the neural tissue to be stimulated;

b. placing a second electrode being an anode in a preferred location near the neural tissue to be stimulated at an optimum distance from the neural tissue to be stimulated, the second electrode located on a first side of the first electrode so that the second electrode is located on a first side of the midline of the spinal column;

c. placing a third electrode in a preferred location near the neural tissue to be stimulated at an optimal distance from the neural tissue to be stimulated, the third electrode located on a second side of the first electrode opposite the second electrode so that the third electrode is located on a second side of the midline of the spinal column opposite the first side of the midline of the spinal column;

d. creating a cathode/anode circuit between the first electrode and the second electrode;

e. creating a cathode/anode circuit between the first electrode and the third electrode;

f. presenting electrical pulses at each cathode/anode circuit created in steps d. and e., the pulses presented at each cathode/anode circuit not overlapping in time during any portion of each pulse whereby an electric field having a frequency of double the frequency of the pulses sent to the electrodes is produced in any area of overlap of the electric fields produced by sending pulses to the cathode/anode circuits formed between the first and second electrodes and the first and third electrodes, respectively.

33. The method of claim 32 wherein step b. includes the step of placing the second electrode at an optimum distance from the first electrode.

34. The method of claim 32 wherein step c. includes the step of placing the third electrode at an optimum distance from the first electrode.

35. The method of claim 32 wherein step f. includes the step of the electrical pulses presented at each cathode/anode circuit being variable in amplitude.

36. The method of claim 32 wherein step f. includes the step of the electrical pulses presented at each cathode/anode circuit being variable in pulse width.

37. The method of claim 32 wherein step f. includes the steps of the pulses presented at each cathode/anode circuit having a pulse width and the pulse width of the pulses presented at each cathode/anode being identical.

38. The method of claim 32 wherein step f. includes the step of the pulses presented at each cathode/anode circuit having an amplitude and the amplitude of the pulses presented at each cathode/anode circuit being identical.

39. A method of controlling a volume of neural tissue stimulation in a spinal column or other neural tissue of a spinal cord, the spinal column having epidural and intrathecal spaces and a dorsal column, the dorsal column having dorsal root entry zones, the spinal column having a midline, the method comprising the steps of:

a. placing a first electrode being a cathode near the midline of the spinal column near the neural tissue to be stimulated;

b. placing a second electrode being an anode in a preferred location near the neural tissue to be stimulated at an optimum distance from the first electrode, the second electrode located on a first side of the first electrode so that the second electrode is located on a first side of the midline of the spinal column;

c. placing a third electrode in a preferred location near the neural tissue to be stimulated at an optimal distance from the first electrode, the third electrode located on a second side of the first electrode opposite the second electrode so that the third electrode is located on a second side of the midline of the spinal column opposite the first side of the midline of the spinal column;

d. creating a cathode/anode circuit between the first electrode and the second electrode;

e. creating a cathode/anode circuit between the first electrode and the third electrode;

f. presenting electrical pulses at each cathode/anode circuit created in steps d. and e., the pulses presented at each cathode/anode circuit not overlapping in time during any portion of each pulse whereby an electric field having a frequency of double the frequency of the pulses sent to the electrodes is produced in any area of overlap of the electric fields produced by sending pulses to the cathode/anode circuits formed between the first and second electrodes and the first and third electrodes, respectively.

40. The method of claim 39 wherein step b. includes the step of placing the second electrode at an optimum distance from the first electrode.

41. The method of claim 39 wherein step c. includes the step of placing the third electrode at an optimum distance from the first electrode.

42. A method of controlling a volume of neural tissue stimulation in a spinal column or other neural tissue of a spinal cord, the spinal column having epidural and intrathecal spaces and a dorsal column, the dorsal column having dorsal root entry zones, the spinal column having a midline, the method comprising the steps of:

a. placing a first electrode being a cathode near the midline of the spinal column near the neural tissue to be stimulated at an optimal distance from the neural tissue to be stimulated and in either the epidural or intrathecal space of the spinal column;

b. placing a second electrode being an anode in a preferred location near the neural tissue to be stimulated at an optimum distance from the neural tissue to be stimulated and in either the epidural or intrathecal space of the spinal column near a dorsal root entry zone of the spinal column, the second electrode located on a first side of the first electrode so that the second electrode is located on a first side of the midline of the spinal column;

c. placing a third electrode being an anode in a preferred location near the neural tissue to be stimulated at an optimal distance from the neural tissue to be stimulated and in either the epidural or intrathecal space of the spinal column near a dorsal root entry zone of the spinal column different from the dorsal root entry zone in step b., the third electrode located on a second side of the first electrode opposite the second electrode so that the third electrode is located on a second side of the midline of the spinal column opposite the first side of the midline of the spinal column;

d. creating a cathode/anode circuit between the first electrode and the second electrode, the first electrode being the cathode and the second electrode being the anode;

e. creating a cathode/anode circuit between the first electrode and the third electrode, the first electrode being the cathode and the third electrode being the anode;

f. presenting electrical pulses at each cathode/anode circuit created in steps d. and e., the pulses presented at each cathode/anode circuit not overlapping in time during any portion of each pulse whereby an electric field having a frequency of double the frequency of the pulses sent to the electrodes is produced in any area of overlap of the electric fields produced by sending pulses to the cathode/anode circuits formed between the first and second electrodes and the first and third electrodes, respectively.

43. The method of claim 42 wherein step b. includes the step of placing the second electrode at an optimum distance from the first electrode.

44. The method of claim 42 wherein step c. includes the step of placing the third electrode at an optimum distance from the first electrode.

45. A method of controlling a volume of neural tissue stimulation in a spinal column or other neural tissue of a spinal column, the spinal column having epidural and intrathecal spaces and a dorsal column, the dorsal column having dorsal root entry zones, the spinal column having a midline, the method comprising the steps of:

a. placing a first electrode being a cathode near the midline of the spinal column near the neural tissue to be stimulated at an optimal distance from the neural tissue to be stimulated;

b. placing a second electrode being an anode in a preferred location near the neural tissue to be stimulated at an optimum distance from the neural tissue to be stimulated, the second electrode located on a first side of the first electrode so that the second electrode is located on a first side of the midline of the spinal column;

c. placing a third electrode being an anode in a preferred location near the neural tissue to be stimulated at an optimal distance from the neural tissue to be stimulated, the third electrode located on a second side of the first electrode opposite the second electrode so that the third electrode is located on a second side of the midline of the spinal column opposite the first side of the midline of the spinal column;

d. connecting the first electrode to a common voltage reference;

e. connecting a different channel of a source of electrical pulses having at least two channels to each of the second and third electrodes, respectively, the source of electrical pulses capable of producing electrical pulses of variable parameters in each channel;

f. producing electrical pulses of variable parameters in each channel, the pulses produced in each channel not overlapping in time during any portion of each pulse.

46. The method of claim 45 wherein step b. includes the step of placing the second electrode at an optimum distance from the first electrode.

47. The method of claim 45 wherein step c. includes the step of placing the third electrode at an optimum distance from the first electrode.

48. An apparatus for stimulating neural tissue in a spinal column comprising:

a) a source of electrical pulses having a plurality of channels through which electrical pulses produced by the source of electrical pulses are passed, the source of electrical pulses producing output pulses in each of the channels, the source of electrical pulses having means for independently changing parameters of the output pulses in each channel;

b) a lead adapted to be implanted near the spinal column, the lead connected to the source of electrical pulses, the lead having a proximal and a distal end and a first axis extending parallel to the spinal column when the lead is implanted near the spinal column, the lead having at least a first, a second and a third electrode located substantially in line near the distal end of the lead, the second electrode being smaller than either the first or third electrodes, the first, second and third electrodes located generally along a second axis that is generally perpendicular to the first axis of the lead, the lead having at least the first and third electrodes each connected to a different channel of the source of electrical pulses and each being an anode, the second electrode being generally centered with respect to the first and third electrodes and also being a cathode so that cathode/anode pairs are formed between each of the first and second electrodes and the second and third electrodes, respectively, the source of electrical pulses producing pulses delivered through the channels to at least the respective first and third electrodes, the pulses through the channels to the respective first and third electrodes not overlapping in time during any portion of each pulse.

49. Apparatus as in claim 48 wherein the source of electrical pulses has means for independently changing timing of the production of each output pulse of each channel with respect to the production of each output pulse of other channels.

50. Apparatus as in claim 48 wherein at least one of the electrodes is generally planar having a first dimension perpendicular to the first axis of the lead and having a second dimension parallel to the first axis of the lead.

51. An apparatus for stimulating neural tissue in a spinal column comprising:

a) a source of electrical pulses having a plurality of channels through which electrical pulses produced by the source of electrical pulses are passed, the source of electrical pulses producing output pulses in each of the channels, the source of electrical pulses having means for independently changing parameters of the output pulses in each channel, the source of electrical pulses having a common voltage reference;

b) a lead adapted to be implanted near the spinal column, the lead connected to the source of electrical pulses, the lead having a proximal and a distal end and a first axis extending parallel to the spinal column when the lead is implanted near the spinal column, the lead having at least a first, a second and a third electrode located substantially in line near the distal end of the lead, the first, second and third electrodes located generally along a second axis that is generally perpendicular to the first axis of the lead, the lead having at least the first and third electrodes each connected to a different channel of the source of electrical pulses and each being an anode, the second electrode being generally centered with respect to the first and third electrodes and also being a cathode so that cathode/anode pairs are formed between each of the first and second electrodes and the second and third electrodes, respectively, the source of electrical pulses producing pulses delivered through the channels to at least the respective first and third electrodes, the pulses through the channels to the respective first and third electrodes not overlapping in time during any portion of each pulse.

52. An apparatus for stimulating neural tissue in a spinal column comprising:

a) a source of electrical pulses having a plurality of channels through which electrical pulses produced by the source of electrical pulses are passed, the source of electrical pulses producing output pulses in each of the channels, the source of electrical pulses having means for independently changing parameters of the output pulses in each channel;

b) a lead adapted to be implanted near the spinal column, the lead connected to the source of electrical pulses, the lead having a proximal and a distal end and a first axis extending parallel to the spinal column when the lead is implanted near the spinal column, the lead having at least a first, a second and a third electrode located substantially in line near the distal end of the lead, the first, second and third electrodes located generally along a second axis that is generally perpendicular to the first axis of the lead, the lead having at least the first and third electrodes each connected to a different channel of the source of electrical pulses and each being an anode, the second electrode being generally centered with respect to the first and third electrodes and also being a cathode so that cathode/anode pairs are formed between each of the first and second electrodes and the second and third electrodes, respectively, the source of electrical pulses producing pulses delivered through the channels to at least the respective first and third electrodes, the pulses through the channels to the respective first and third electrodes not overlapping in time during any portion of each pulse, the first, second and third electrodes being generally planar and having a first dimension perpendicular to the first axis of the lead and having a second dimension parallel to the first axis of the lead, wherein the second electrode has a smaller second dimension than the second dimensions of either the first or third electrodes.

53. Apparatus as in claim 52 wherein the second electrode has a predetermined first dimension and wherein the first and third electrodes have a larger first dimension than the first dimension of the second electrode.

* * * * *

UNITED STATES PATENT AND TRADEMARK OFFICE
CERTIFICATE OF CORRECTION

PATENT NO. : 5,643,330
DATED : July 1, 1997
INVENTOR(S) : Holsheimer et al

It is certified that error appears in the above-identified patent and that said Letters Patent is hereby corrected as shown below:

On the title page item [57], line 7, "mater" should be "matter" ; and line 16, "by the each" should be "by each"

Col. 4, Line 21, "stimulation it is" should be "stimulation"
Col. 5, Line 8, "min." should be "mm"
Col. 8, Line 16, "391" should be "39I"

Signed and Sealed this

Twenty-first Day of December, 1999

Attest:

Q. TODD DICKINSON

*Attesting Officer*   *Acting Commissioner of Patents and Trademarks*